United States Patent
Joseph et al.

(10) Patent No.: US 11,666,603 B2
(45) Date of Patent: Jun. 6, 2023

(54) METHODS AND COMPOSITIONS FOR PURIFICATION OR ISOLATION OF MICROVESICLES AND EXOSOMES

(71) Applicant: Exopharm Limited, Doncaster East (AU)

(72) Inventors: Chacko Joseph, Blackburn (AU); Jim Palmer, Blackburn (AU); Ian Dixon, Blackburn (AU); Gregor Lichtfuss, Blackburn (AU)

(73) Assignee: EXOPHARM LIMITED, Doncaster East (AU)

( * ) Notice: Subject to any disclaimer, the term of this patent is extended or adjusted under 35 U.S.C. 154(b) by 939 days.

(21) Appl. No.: 16/471,191

(22) PCT Filed: Dec. 22, 2017

(86) PCT No.: PCT/AU2017/051460
§ 371 (c)(1),
(2) Date: Jun. 19, 2019

(87) PCT Pub. No.: WO2018/112557
PCT Pub. Date: Jun. 28, 2018

(65) Prior Publication Data
US 2020/0023012 A1    Jan. 23, 2020

(30) Foreign Application Priority Data
Dec. 23, 2016    (AU) ................................ 2016905369

(51) Int. Cl.
*A61K 35/28* (2015.01)
*B01D 15/38* (2006.01)
(Continued)

(52) U.S. Cl.
CPC .............. *A61K 35/28* (2013.01); *B01D 15/08* (2013.01); *B01D 15/20* (2013.01); *B01D 15/362* (2013.01);
(Continued)

(58) Field of Classification Search
CPC ........ A61K 35/28; A61K 35/66; A61K 35/30; A61K 9/127; B01D 15/08; B01D 15/20;
(Continued)

(56) References Cited

U.S. PATENT DOCUMENTS 6,899,863 B1    5/2005  Dhellin et al.
11,202,805 B2   12/2021 Joseph et al.
(Continued)

FOREIGN PATENT DOCUMENTS

RU    2556825 C1      7/2015
WO    2008039136 A1   4/2008
(Continued)

OTHER PUBLICATIONS

"Nucleophile," Chemistry Learner. Available at <https://www.chemistrylearner.com/nucleophile.html>, accessed Jun. 28, 2021. (Year: 2021.
(Continued)

*Primary Examiner* — Emmanuel E Duke
(74) *Attorney, Agent, or Firm* — Kilpatrick Townsend & Stockton LLP

(57) ABSTRACT

The invention relates to the isolation or extraction of exosomes.

27 Claims, 17 Drawing Sheets

(51) Int. Cl.
| | |
|---|---|
| *B01D 15/08* | (2006.01) |
| *B01D 15/20* | (2006.01) |
| *B01J 20/26* | (2006.01) |
| *B01J 20/32* | (2006.01) |
| *C12N 5/00* | (2006.01) |
| *B01D 15/36* | (2006.01) |
| *B01J 39/26* | (2006.01) |
| *C07K 14/435* | (2006.01) |

(52) U.S. Cl.
CPC ..... *B01D 15/3823* (2013.01); *B01D 15/3828* (2013.01); *B01J 20/262* (2013.01); *B01J 20/3274* (2013.01); *B01J 39/26* (2013.01); *C12N 5/00* (2013.01); *B01D 2015/3838* (2013.01); *C07K 14/435* (2013.01)

(58) Field of Classification Search
CPC .............. B01D 15/362; B01D 15/3823; B01D 15/3828; B01D 2015/3838; B01J 20/262; B01J 20/3274; B01J 39/26; C12N 5/00; C12N 5/0619; C12N 2509/00; C07K 14/435; C12M 47/10; A61P 43/00; G01N 33/5076; C12Q 1/24
See application file for complete search history.

(56) References Cited

U.S. PATENT DOCUMENTS

| | | | | |
|---|---|---|---|---|
| 2004/0242561 | A1* | 12/2004 | Ji | A61K 47/55 514/211.07 |
| 2005/0277117 | A1* | 12/2005 | Ofer | G16B 45/00 435/7.1 |
| 2010/0099163 | A1* | 4/2010 | Andersson | B01J 20/3272 435/308.1 |
| 2013/0273544 | A1* | 10/2013 | Vlassov | G01N 33/5076 435/6.12 |
| 2015/0024411 | A1* | 1/2015 | Stadler | G01N 33/56966 435/325 |
| 2015/0192571 | A1* | 7/2015 | Ghosh | C12Q 1/6886 435/7.1 |
| 2016/0202248 | A1 | 7/2016 | Ly et al. | |
| 2016/0216253 | A1 | 7/2016 | Balaj et al. | |
| 2021/0128632 | A1 | 5/2021 | Joseph et al. | |
| 2021/0245074 | A1 | 8/2021 | Lichtfuss et al. | |
| 2022/0296646 | A1 | 9/2022 | Joseph et al. | |

FOREIGN PATENT DOCUMENTS

| | | | | |
|---|---|---|---|---|
| WO | 2010065765 | A2 | 6/2010 | |
| WO | 2013/124474 | A2 | 8/2013 | |
| WO | 2016005363 | A1 | 1/2016 | |
| WO | 2016007755 | A1 | 1/2016 | |
| WO | WO-2016007755 | A1 * | 1/2016 | ......... C12N 15/1006 |
| WO | 2014010571 | A1 | 6/2016 | |
| WO | 2017/197399 | A1 | 11/2017 | |
| WO | 2018/112557 | A1 | 6/2018 | |

OTHER PUBLICATIONS

Final Office Action in U.S. Appl. No. 17/147,033, dated Jul. 6, 2021, 11 pages.
Non-Final Office Action in U.S. Appl. No. 17/147,033, dated May 27, 2021, 10 pages.
Arora, J. S., et al., "Spatially directed vesicle capture in the ordered pores of breath-figure polymer films", Soft Matter, 2015, 11, pp. 5188-5191.
Chen, Chihchen , et al., "Microfluidic isolation and transcriptome analysis of serum microvesicles", Lab Chip, 2010, 10, pp. 505-511.
Greening, David W., et al., "A Protocol for Exosome Isolation and Characterization: Evaluation of Ultracentrifugation, Density-Gradient Separation, and Immunoaffinity Capture Methods", Proteomic Profiling: Methods and Protocols, Methods in Molecular Biology, vol. 1295, pp. 179-209.
Heinemann, Mitja L., et al., "Benchtop isolation and characterization of functional exosomes bysequential filtration", Journal of Chromatography A, 1371 (2014), pp. 125-135.
Kim, Gahee , et al., "Noble Polymeric Surface Conjugated with Zwitterionic Moieties and Antibodies for the Isolation of Exosomes from Human Serum", American Chemical Society, Bioconjugate Chem., 2012, 23, pp. 2114-2120.
Lane, Rebecca E., et al., "Analysis of exosome purification methods using a model liposome system and tunable-resistive pulse sensing", Scientific Reports, 5:7639, (2015), 8 pages.
Liga, A. , et al., "Exosome isolation: a microfluidic road-map", Lab Chip, 2015, 15, pp. 2388-2394.
Nordin, Joel Z., et al., "Ultrafiltration with size-exclusion liquid chromatography for high yield isolation of extracellular vesicles preserving intact biophysical and functional properties", Nanomedicine: Nanotechnology, Biology, and Medicine 11 (2015), pp. 879-883.
Rani, Sweta , et al., "Mesenchymal Stem Cell-derived Extracellular Vesicles: Toward Cell-free Therapeutic Applications", The American Society of Gene & Cell Therapy, vol. 23, No. 5, (2015), pp. 812-823.
Raposo, Graca , et al., "Extracellular vesicles: Exosomes, microvesicles, and friends", J. Cell Biol., vol. 200, No. 4, pp. 373-383.
Rider, Mark A., et al., "ExtraPEG: A Polyethylene Glycol- Based Method for Enrichment of Extracellular Vesicles", Scientific Reports, 6:23978, (2016), 15 pages.
Sakudo, Akikazu , et al., "Use of anionic polymer, poly(methyl vinyl ether-maleic anhydride)-coated beads for capture of respiratory syncytial virus", Bioorganic & Medicinal Chemistry Letters 19 (2009) 4488-4491.
Urbanelli, Lorena , et al., "Signaling Pathways in Exosomes Biogenesis, Secretion and Fate", Genes (2013), 4, pp. 152-170.
Van Der Pol, E. , et al., "Optical and non-optical methods for detection and characterization of microparticles and exosomes", Journal of Thrombosis and Haemostasis (2010); 8: 2596-2607.
Zeringer, Emily , et al., "Strategies for Isolation of Exosomes", Cold Spring Harb Protoc; doi:10.1101/pdb.top074476, 6 pages.
Machine Translation of RU 2556825, 6 pages.
International Patent Application No. PCT/AU2017/051460, Written Opinion, dated Jan. 29, 2018, 9 pages.
International Patent Application No. PCT/AU2017/051460, International Search Report, dated Jan. 29, 2018, 5 pages.
International Patent Application No. PCT/AU2019/050625, International Search Report and Written Opinion, dated Aug. 29, 2019, 13 pages.
U.S. Appl. No. 17/832,232, Non-final Office Action, dated Jul. 29, 2022, 9 pages.

* cited by examiner

METHODS AND COMPOSITIONS FOR PURIFICATION OR ISOLATION OF MICROVESICLES AND EXOSOMES

CROSS REFERENCE TO RELATED APPLICATIONS

This is a National Phase entry of International Application No. PCT/AU2017/051460, filed Dec. 22, 2017, which claims priority to Australian Patent Application No. AU 2016905369, filed Dec. 23, 2016, the disclosures of which are incorporated herein by reference in their entireties.

FIELD OF THE INVENTION

The invention relates to cellular microvesicles, particularly exosomes, to molecular modelling and to chromatographic methods for separation and isolation of molecules including ion exchange chromatography.

BACKGROUND OF THE INVENTION

Reference to any prior art in the specification is not, and should not be taken as, an acknowledgment or any form of suggestion that this prior art forms part of the common general knowledge in Australia or any other jurisdiction.

Microvesicles are a heterogeneous collection of biological structures bound by membranes. These structures have a lipid bilayer and they may reside within a cell or in an extracellular environment. Microvesicles range in size from about 20 nm to 1000 nm.

Exosomes are small lipid bilayer vesicles, secreted by multiple cell types, and ranging in diameter from 20 to ~150 nm (as determined by electron microscopy (EM)). Unlike other cell-derived microvesicles, exosomes are formed within the intracellular space and then secreted by the cell (Raposo and Stoorvogel, 2013).

The lipid composition of exosomes is distinct from that of the cell of origin, but is still somewhat characteristic of the cell type from which they originate. In addition, exosomes show some common lipid features independently of their origin (Urbanelli et al., 2013).

Depending on their origin, exosomes may contain a wide variety of "cargo", including but not limited to peptides, proteins, lipids, transcription regulators, messenger RNA (mRNA), noncoding RNA (ncRNA) and double stranded DNA (dsDNA).

Exosomes are now considered as a means by which an originating cell (i.e. the cell from which the exosome originates) can communicate with a target cell, in situations such as neuronal synapses, immune regulation, angiogenesis, tissue regeneration and epigenetic modulation. Such communication can be localized or remote. Indeed, exosomes from mother's milk can modulate immune and other functions in the new-born. Such communication can even be cross-species, for example, but not limited to, bovine milk exosomes modulating immune and other functions in humans.

Exosomes can be sourced from various biofluids, including saliva, urine, blood, blood plasma, (breast) milk, synovial fluid ascites fluid, sap, and fruit extracts.

In summary of the above, it appears that the unique characteristics of exosomes is driven by their size, cell uptake by endocytosis, their "cargo", and that they deliver "messages" that become biologically active in the target cell.

There is mounting evidence that exosomes may play a role in the onset and perpetuation of various diseases. Exosomes collected from biological samples can provide diagnostic information on the current state of a disease. The concentration of RNA in exosomes can be up to 60 times greater than that extracted directly from body fluids such as blood, driving the potential for their utility in diagnostics. For example, identification of oncogenic RNA signature within exosomes isolated from human fluids could potentially yield a diagnosis of an abnormal state well before invasive cancer develops.

Recently it has been shown that the function of therapeutic mesenchymal type cells is not dependent upon the cell itself, but rather paracrine factors produced by the cell, including exosomes, establishing that exosomes are one part of the circulating cell secreted factors that can mediate the effect seen in some cell therapies in a cell-free manner (Rani et al., 2015).

Therapeutically useful exosomes collected from the conditioned media of cells undergoing in vitro culture can also be used as a cell-free therapeutic, but there is a need for robust, flexible method of isolation from their source fluids (Chen et al., 2010).

In addition, exosomes could provide a natural delivery vehicle packed with therapeutic proteins and RNA when cell-based expression systems are tailored specifically.

Exosomes are invisible under normal optical microscope. Technologies used for detection of these ultramicroscopic particles like exosomes and microvesicles include electron microscopy (EM), flow cytometry, dynamic light scattering (DLS), and nanoparticle tracking analysis (NTA). It has been reported that, depending on the method used, the reported absolute number of extracellular vesicles in a liter of blood can vary by as much as five orders of magnitude (van der Pol et al., 2010).

While exosomes are abundant and expected to be useful either in a diagnostic or therapeutic sense, the means to isolate and purify exosomes has limited their clinical application to date.

In general, existing methods for exosome isolation are characterized by two groups:
(i) affinity capture due to some (possibly unique) selective external feature of the vesicle (e.g. glycoprotein marker, transmembrane proteins like tetraspanins (CD9, CD63, CD81, and CD82) and MHC class I and II, and cytosolic proteins like heat shock proteins (HSP-70 and HSP-90))
(ii) isolation or purification based on some biophysical property of the exosome (e.g. size, density, zeta potential, highly curved surface that contains lipid-packing defects, membrane curvature sensors)

The limitations of these techniques are set forth in the table below

| Method | Application | Limitations |
| --- | --- | --- |
| Ultra-centrifugation (UC) | Differential centrifugation Density gradient centrifugation (Greening et al., 2015) | Scalability, operational complexity, EV aggregation |
| Polymer assisted precipitation | Polyethylene glycol based precipitation (Rider et al., 2016) | Co-precipitation of protein contaminants, need for removal of polymers after precipitation |
| Immunoaffinity capture | CD9, CD63, CD81 and EpCam antibody based capture (Greening et al., 2015) (U.S. patent application 20150010913) | Isolation of sub-population of exosomes, lack of single standard maker for exosome, issues with removal of antibody bound to exosome |

-continued

| Method | Application | Limitations |
|---|---|---|
| Tangential flow filtration | Sequential filtration (Heinemann et al., 2014) | Requirement of additional steps to further purify exosomes. |

US2013/0273544 (Vlassov) and US2015/0192571 (Ghosh) both disclose the use of polymers including poly ethylene glycol and certain polysaccharides as volume excluding polymers for the precipitation of microvesicles from a solution. US20160216253 discloses the use of heparin for isolation of extracellular vesicles.

There is a need for an improved method for isolation of exosomes, in particular a method that provides for an improved yield of exosomes, and that is scalable for pharmaceutical grade manufacture or production of exosomes, and that avoids other limitations of the prior art discussed above.

SUMMARY OF THE INVENTION

The invention seeks to address one or more of the above mentioned needs or limitations and in one embodiment provides a method for obtaining an isolate or composition of exosomes. The method includes the following steps:
  providing a liquid that includes exosomes;
  providing a substrate having a surface, the surface having an array of exosome-binding ligands;
    wherein each ligand is in the form of an anionic or electron-rich group; and
    wherein the array of exosome-binding ligands enables exosomes to bind to the substrate;
  contacting the liquid with the substrate in conditions enabling the binding of exosomes to the exosome-binding ligands;
  separating the substrate from the liquid;
  thereby obtaining an isolate or composition of exosomes.

In another embodiment, there is provided a method for obtaining an isolate or composition of exosomes. The method includes the following steps:
  providing a liquid that includes exosomes;
  providing a substrate having a surface, the surface having an array of exosome-binding ligands;
    wherein each ligand is in the form of an anionic or electron-rich group at pH of 4-8, preferably pH 5 to 8, selected from the group consisting of $CO_2H$, $CH_2OH$, $CH_2OSO_3H$, $B(OH)_2$, and $CH_2OP(O)(OH)_2$, or those groups in ionized form as dictated by their relevant pKa;
    wherein each ligand is spaced apart from other ligands by about 4-5 Å;
    wherein the array of exosome-binding ligands enables exosomes to bind to the substrate;
  contacting the liquid with the substrate in conditions enabling the binding of exosomes to the exosome-binding ligands;
  separating the substrate from the liquid;
  thereby obtaining an isolate or composition of exosomes.

In another embodiment there is provided a method for obtaining an isolate or composition of microvesicles. The method includes the following steps:
  providing a liquid that includes microvesicles;
  providing a substrate having a surface, the surface having an array of exosome-binding ligands;
    wherein each ligand is in the form of an anionic or electron-rich group; and
    wherein the array of exosome-binding ligands enables microvesicles to bind to the substrate;
  contacting the liquid with the substrate in conditions enabling the binding of microvesicles to the exosome-binding ligands;
  separating the substrate from the liquid;
  thereby obtaining an isolate or composition of microvesicles.

In another embodiment, there is provided a method for obtaining an isolate or composition of microvesicles. The method includes the following steps:
  providing a liquid that includes microvesicles;
  providing a substrate having a surface, the surface having an array of exosome-binding ligands;
    wherein each ligand is in the form of an anionic or electron-rich group at pH of 4-8, preferably pH 5 to 8, selected from the group consisting of $CO_2H$, $CH_2OH$, $CH_2OSO_3H$, $B(OH)_2$, and $CH_2OP(O)(OH)_2$, or those groups in ionized form as dictated by their relevant pKa.
    wherein each ligand is spaced apart from other ligands by about 4-5 Å
  wherein the array of exosome-binding ligands enables microvesicles to bind to the substrate;
  contacting the liquid with the substrate in conditions enabling the binding of microvesicles to the exosome-binding ligands;
  separating the substrate from the liquid;
  thereby obtaining an isolate or composition of microvesicles.

The invention also provides an apparatus or device including a substrate as described above that enables execution of the above described method.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION OF THE EMBODIMENTS

Figure 1:
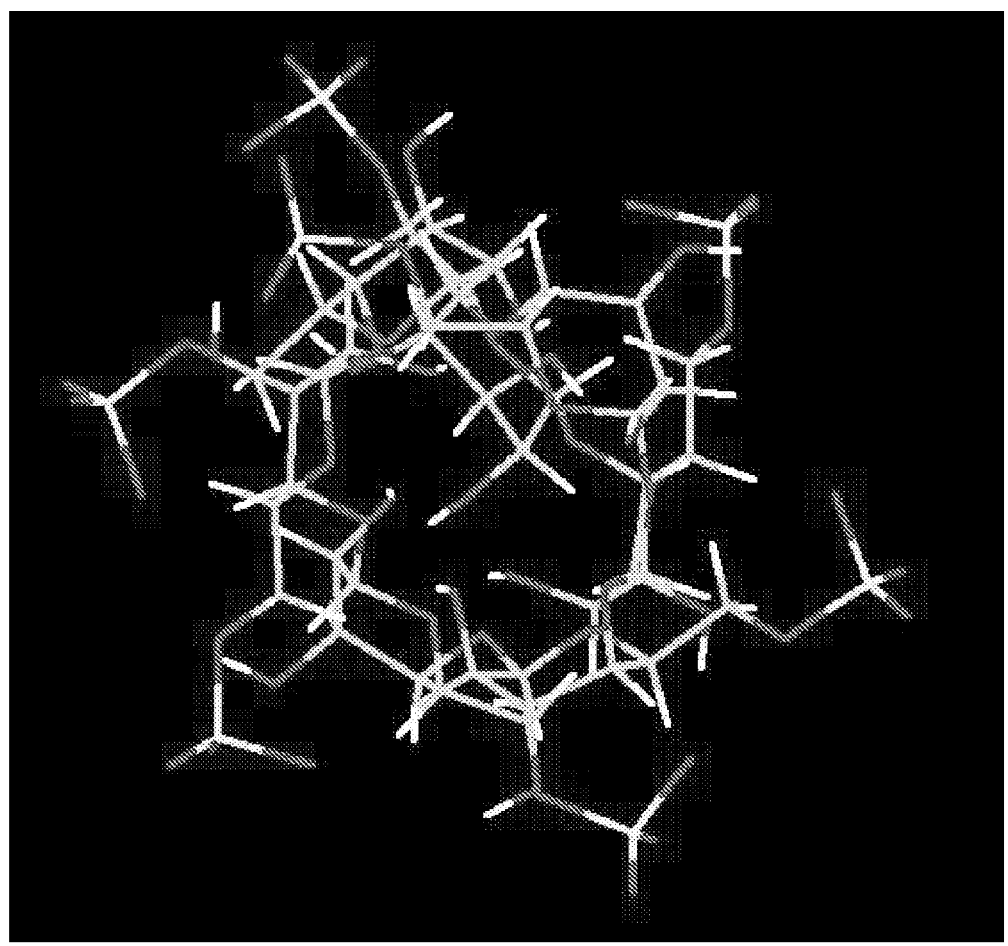
FIG. 1—Predicted structure of cellulose/cellufine sulfate: (A) projected end on view; and (B) side on view; and cellulose/cellufine phosphate: (C) projected end on view; and (D) side on view.

The invention is concerned with the design of reagents and methods for improvements in the isolation of extracellular vesicles, especially exosomes, from biological sources including conditioned cell media, in vivo fluids, tissues and biopsies, and extracts or fractions or isolates thereof. In particular, the invention is concerned with reagents and methods that provide for improved capture of extracellular vesicles from a source and improved release, resulting in reproducibly higher yields of extracellular vesicles. As described herein, the inventors have determined heretofore unknown characteristics required in substances for obtaining improved yields of extracellular vesicles, in particular, exosomes, from biological sources. This work enables the selection and or design of substances for use in methods of isolating microvesicles and exosomes.

"Extracellular vesicles (EVs) or micro vesicles (MVs)" generally refer to a heterogeneous in vivo collection of membrane bound biological structures having a diameter from about 20 to 1000 nm.

"Exosome" generally refers to a vesicle having a lipid bilayer and a diameter of about 20 to 200 nm as measured by EM.

"Binding efficiency" generally refers to a measure of the proportion of exosomes bound by a substrate. It is the difference of the amount of exosomes remaining in a sample after application of the method of the invention and the amount of exosomes in a sample before application of the method of the invention.

"Elution efficiency" generally refers to a measure of the proportion of exosomes eluted from a substrate. It is the difference of the amount of exosomes in the eluate after elution according to the method of the invention and the theoretical amount of exosomes bound to the substrate.

"Yield" generally refers to the number of exosomes released from the eluate as a proportion of the total number of exosomes before the application of the method of the invention.

"Comprise" and variations of the term, such as "comprising", "comprises" and "comprised", are not intended to exclude further additives, components, integers or steps.

In a first embodiment the invention provides a method for obtaining a composition or an isolate of exosomes. The method includes the following steps:
  providing a liquid that includes exosomes;
  providing a substrate having a surface, the surface having an array of exosome-binding ligands;
    wherein each ligand is in the form of an anionic or electron-rich group; and
    wherein the array of exosome-binding ligands enables exosomes to bind to the substrate;
  contacting the liquid with the substrate in conditions enabling the binding of exosomes to the exosome-binding ligands;
  separating the substrate from the liquid;
  thereby obtaining a composition or an isolate of exosomes.

In another embodiment there is provided a method for obtaining an isolate or composition of microvesicles. The method includes the following steps:
  providing a liquid that includes microvesicles;
  providing a substrate having a surface, the surface having an array of exosome-binding ligands;
    wherein each ligand is in the form of an anionic or electron-rich group; and
    wherein the array of exosome-binding ligands enables microvesicles to bind to the substrate;
  contacting the liquid with the substrate in conditions enabling the binding of microvesicles to the exosome-binding ligands;
  separating the substrate from the liquid;
  thereby obtaining an isolate or composition of microvesicles.

According to this embodiment, a substrate is provided having a surface. An array of exosome-binding ligands is provided on the surface so as to enable contact of the exosome-binding ligands with the outer surface or membrane of a microvesicle when the liquid is contacted with the substrate.

The array of exosome-binding ligands is more or less an ordered arrangement of exosome-binding ligands on the substrate surface. Typically the array takes the form of a plurality of exosome-binding ligands that are positioned across at least a part or region of the substrate surface.

An array may be in the form of a planar array or a linear array.

A planar array generally extends in 2 dimensions so as to define an area. A planar array may generally include a region of exosome-binding ligands having a density of about 1 to 10 ligands per $nm^2$, preferably about 5 ligands per $nm^2$. This spacing can be determined for example by atomic force microscopy. Other regions of the array may have a higher or lower density of exosome-binding ligands. Thus in one embodiment there is provided a method for obtaining a composition or an isolate of exosomes or microvesicles. The method includes the following steps:
  providing a liquid that includes exosomes;
  providing a substrate having a surface, the surface having an planar array of exosome-binding ligands;
    wherein each ligand is in the form of an anionic or electron rich group; and
    wherein the planar array of exosome-binding ligands enables exosomes to bind to the substrate;
  contacting the liquid with the substrate in conditions enabling the binding of exosomes to the exosome-binding ligands;
  separating the substrate from the liquid;
  thereby obtaining a composition or an isolate of exosomes,
  wherein the planar array preferably includes a region of exosome-binding ligands having a density of about 1 to 10 ligands per $nm^2$, more preferably about 5 ligands per $nm^2$.

A linear array generally extends in one dimension. In one embodiment, a linear array may be formed where exosome-binding ligands are provided on a polymer that has a generally linear arrangement on a substrate surface. In another embodiment, in use, the polymer may extend from the substrate into a solvent. In a linear array, the exosome-binding ligands are generally provided in a range of from 1 to 5 ligands per nm, preferably about 2 ligands per nm. This spacing can be determined for example by atomic force microscopy or mass spectrometry. Thus in another embodiment there is provided a method for obtaining a composition or an isolate of exosomes or microvesicles. The method includes the following steps:

providing a liquid that includes exosomes;
providing a substrate having a surface, the surface having a linear array of exosome-binding ligands;
   wherein each ligand is in the form of an anionic or electron rich group; and
   wherein the linear array of exosome-binding ligands enables exosomes to bind to the substrate;
contacting the liquid with the substrate in conditions enabling the binding of exosomes to the exosome-binding ligands;
separating the substrate from the liquid;
thereby obtaining a composition or an isolate of exosomes,
wherein the exosome-binding ligands are preferably provided in a range of from 1 to 5 ligands per nm, more preferably about 2 ligands per nm.

In further embodiments, it has been found that a substrate that has an array of exosome-binding ligands distributed across the substrate surface that interfaces with a microvesicle outer membrane surface, in which an exosome-binding ligand is spaced no more than about 3.5 to 10 angstroms apart from another exosome-binding ligand, forms a highly efficient exosome-binding surface. As explained further below, where the array is provided to the substrate surface by one or more polymers that include the exosome-binding ligands, the measurement of 3.5 to 10 angstroms, preferably greater than 2 angstroms, particularly about 4 to 6 angstroms, with reference to the spacing of exosome-binding ligands, refers to the spacing observed in the lowest energy state of the polymer as determined by the methods exemplified herein.

As described further herein, the invention provides a structural model of an arrangement of exosome-binding ligands that predicts substrates that are highly efficient exosome binders. According to the model, highly efficient exosome binders are generally substrates that have anionic or electron rich groups spaced apart by about 4 to 6 Angstroms as measured according to the methodology on which the structural model is based. The invention enables one to predict the binding efficiency of a substrate for an exosome or microvesicle through the identification of anionic or electron rich groups and by modelling the structure of the substrate utilizing the methodology for the derivation of the structural model herein.

Preferably an exosome-binding ligand is spaced more than 2 angstroms apart from another exosome-binding ligand. More preferably an exosome-binding ligand is spaced 3.5 to 6, or 4 to 6 angstroms, more preferably 3.5, 4, 5 or 6 angstroms apart from another exosome-binding ligand in the array.

Typically the majority of ligands, preferably 60%, or 70% or 80%, more preferably 90%, still more preferably 95%, 96%, 97%, 98% or 99% of ligands are spaced more than 2 angstroms, and no more than about 10 angstroms apart, preferably 3.5 to 6, or 4 to 6 angstroms from another ligand in the array.

According to the invention, the arrangement of the exosome-binding ligands in the array may have various levels of order. In one embodiment, there may be a very high order of arrangement of exosome-binding ligands within the array. For example, each ligand may be spaced apart from other ligands in the array by a precise distance of 4 angstroms. Further, the position of each ligand, and/or the spaces between ligands may define a particular pattern. In such a higher order of arrangement, generally all of the ligands are evenly spaced apart in the array. As described herein, it has been found that a surface having an array of exosome-binding ligands with a higher order of arrangement generally has a reproducibly higher exosome or microvesicle binding efficiency.

In other embodiments, there may be a lower order of arrangement of exosome-binding ligands within the array. For example, the majority, but not all of the ligands may be spaced apart from each other by more than 2 angstroms, and no more than about 10 angstroms apart, preferably 3.5 to 6, or 4 to 6 angstroms from another ligand in the array. Further, of this majority of ligands, there may be variability as between the spacing of these ligands in the array. For example, some ligands may be spaced apart from others by 3.5 angstroms, others by 4 angstroms, others by 5 angstroms, others by 6 angstroms. In such an arrangement, the position of each ligand, and/or the spaces between the ligands may not define a discernible pattern. However, it has been found that such a lower order array has useful binding efficiency for binding exosomes.

As would be appreciated, the extent of order amongst exosome-binding ligands can be thought of as a local-order and meta-order. By this we mean that looking at the array of exosome-binding ligands at a distance there might seem to be a randomness to the location of the ligands (i.e. they are not in clear orthogonal arrays) (meta-order) yet the mean distance between ligands might be relatively tightly distributed around a mean value (local-order). In this invention it is discovered that a higher-order of local-order is preferred whereas the extent of meta-order is of less importance. Therefore, in certain embodiments, the array may include regions of meta-order, provided that the array contains at least one region of local-order.

An array may be formed on the substrate surface by a variety of methods. A higher order array may be formed by deposition of exosome-binding ligands at precise positions on the substrate surface. Examples include crystalline silicon, ceramic or polymer surfaces using lithography, plasma immersion ion implantation and deposition (PIII&D), atomic force microscope, laser, electrical etching, low-density plasma reactive ion etching, wet etching, electron microscope or other means known to produce a functionalized surface containing exosome-binding ligands.

In another embodiment, an array may be printed on a substrate surface. Examples include functionalizing the substrate surface with a chemical pad and then further derivatizing such pads with exosome-binding ligand moieties which are now chemically bound to such pads.

In another embodiment, the array is provided to the substrate surface by one or more polymers that include the exosome-binding ligands. In this embodiment, the substrate may be integrally formed from the polymer thereby forming a substrate surface. Additionally, or alternatively, the polymer may be coupled or otherwise bound to the substrate, thereby forming a substrate surface, for example via biotin/streptavidin binding.

In embodiments where the substrate is formed from the polymer, the substrate surface may be treated so as to activate that polymer for formation of exosome-binding ligands on the polymer.

In other embodiments, a polymer including exosome-binding ligands is coated onto the substrate, thereby forming exosome-binding ligands on the substrate surface.

As stated above, and described in detail further herein, where the exosome-binding ligands are to be provided in an array by one or more polymers, those polymers are selected according to whether, at the lowest energy, the ligands they present are observed in silico to be spaced apart from each other by more than 2 angstroms, and no more than about 10 angstroms apart, preferably 3.5 to 6 angstroms, or 4 to 6 angstroms apart. Briefly, the in silico observation is derived from subjecting a sub structural unit (typically hexamer to dodecamer, but may be larger) of a polymer, complete with anionic or electron-rich groups to geometry-minimization calculations (MM+algorithm) so as to display a most stable (lowest energy) three-dimensional structure, and therefore the structure likely to be involved in exosome binding. The distance between ligands can then be measured in silico to determine the likelihood of binding to exosomes. When the energy-minimized structure of the modeled oligomer bears a suitable number of ligand pairs wherein the separation of electron-rich or anionic ligand pairs is of a distance from 2 to 10 angstroms, then the polymer that this modeled oligomer represents will be suitable for binding exosomes or microvesicles according to this invention.

Thus in another embodiment there is provided a method for obtaining a composition or an isolate of exosomes or microvesicles. The method includes the following steps:

- providing a liquid that includes exosomes or microvesicles;
- providing a substrate having a surface, the surface having an array of exosome-binding ligands;
  - wherein each ligand is in the form of an anionic group or electron rich group; and
  - wherein the array of exosome-binding ligands enables exosomes to bind to the substrate;
- contacting the liquid with the substrate in conditions enabling the binding of exosomes or microvesicles to the exosome-binding ligands;
- separating the substrate from the liquid;
- thereby obtaining a composition or an isolate of exosomes or microvesicles, wherein the exosome-binding ligands are observed in silico to be spaced apart from each other by more than 2 angstroms, and no more than about 10 angstroms apart, preferably 3.5 to 6 angstroms, preferably 4 to 6 angstroms apart in an energy minimization model described herein.

The order of an array formed from exosome-binding ligands provided on one or more polymers is generally dependent on the heterogeneity of the polymers with respect to the order of monomers within each polymer and the length of each polymer. Preferably, the polymers for use in the invention have little heterogeneity, or otherwise, more or less, homogeneity with respect to the monomer order and polymer length. Preferably the polymers are linear.

In this regard, synthetic polymers, rather than polymers derived from natural or biological sources are preferred. This is because polymers from biological sources, such as certain polysaccharides, have significant heterogeneity with respect to either polymer length, branching, monomer order and even monomer functionalization. As described herein, this heterogeneity generally contributes to a lower efficiency of binding of exosomes or microvesicles and a lower exosome or microvesicle yield. Therefore, in one embodiment the polymer is not an unfractionated or heterogeneous natural or biological source, particularly of heparin.

More preferably, with respect to monomer content, the polymers have a uniform order of monomers, particularly where the polymer comprises different monomer species, and wherein only some of the monomer species contain exosome-binding ligands. It is particularly important that the uniformity of monomer order creates a uniformity in the spacing of the exosome-binding ligands that are presented to the outer membrane surface of the exosome or microvesicle. This generally requires that there is a uniform stereochemistry of exosome-binding ligands for interaction with the exosomes or microvesicles.

It is preferred that at least 25% of monomers forming a polymer, preferably 50%, 60%, 70%, 80%, 90%, 95%, 96%, 97%, 98% of monomers forming a polymer have an exosome-binding ligand that is arranged on the substrate surface to enable binding to an exosome or microvesicle outer membrane.

It is particularly preferred that all of the monomers forming a polymer present exosome-binding ligands that are spaced about 3.5 to 6 angstroms, 4 to 6 angstroms, preferably, 3.5, 4, 5 or 6 angstroms from each other to the outer membrane surface of an exosome or microvesicle.

In certain embodiments where a polymer consists of more than one monomeric species, a species may provide one type of exosome-binding ligand and another monomeric species may provide another type of exosome-binding ligand.

Further, depending on the length of a monomer species, a monomer species may provide more than one exosome-binding ligand (which may be the same or different), provided that the ligands provided on the monomer species, in their presentation to the exosome or microvesicle outer surface are spaced about 3.5 to 6 angstroms, or 4 to 6 angstroms, preferably, 3.5, 4, 5 or 6 angstroms from each other.

A surprising finding of the invention is that exosomes and micro-vesicles can be separated from other components of an in vivo or in vitro formed biological fluid on the basis of charge, and in particular, a positive charge on the exosome or microvesicle. This is surprising because it had been generally understood that most cell membranes and lipid bilayers have a net negative charge, particularly arising from lipid polar head groups, membrane sugars and proteins that are generally negatively charged at physiological pH.

The exosome-binding ligand utilized in the above described embodiments is in the form of, or consists of an anion or an electron rich group. Exosomes are generally stable at physiological pH of 7.4+/−1-1.5. Therefore, the exosome-binding ligand is generally an anion, or otherwise an electron rich group at a pH of about 4 to 8 or 5 to 8.

The exosome-binding ligand may be an inorganic or organic anion or electron rich group. Examples of inorganic anions include anions that contain a sulfur, selenium, boron, nitrogen or phosphorus atom and include sulfates, selenates, phosphates, phosphonates, phosphinates.

Preferably the ligand is an organic anion or electron rich group. Examples include sulfated alcohols and amines, amides, sulfonamides, carboxylate groups, alcohols, ethers, anhydrides, selenates, imides, acylsulfonamides, phosphonates, phosphinates, phosphates, etc.

In one embodiment, an array of exosome-binding ligands according to the invention may be a combination of organic and inorganic anions or electron rich groups.

An important finding of the invention as described herein is that where a polymer is utilized to provide the array of exosome-binding ligands, the polymer is selected on the basis of its capacity to present or display a uniformly spaced plurality of exosome-binding ligands to a microvesicle outer membrane surface, rather than on the basis of some other characteristic of the polymer backbone. In this regard the invention is distinguished from other approaches, described previously, which have utilized polymers to precipitate microvesicles from solution. Those approaches have typically selected polymers on the basis of aqueous solubility and volume exclusion characteristics. Exemplary polymers utilized in these approaches are polyethylene glycol [US2013/0273554 and US2013/0337440] and polysaccharides [US20150192571].

According to the invention, the polymer may be a polysaccharide, polyethylene terephthalate or peptide with side chains suitable for derivatization with anionic or electron-rich groups, such as polyaspartic acid, polyserine, polythreonine, polyasparagine, nucleic acid or other organic molecule, such as polyethers, (PEGS), sulfated polyvinyl alcohols, polyphenols, polyphenylboronic acids, or other polyaromatics or polyheteroaromatics, preferably synthetic.

In embodiments where the polymer is derived from a natural or biological source, and the polymer is known to have significant source-dependent heterogeneity, specifically with respect to polymer length, monomer content and order, it is particularly preferred to fractionate the natural or biological source so as to decrease heterogeneity and increase homogeneity for a polymer of desired length, monomer content or order.

Typically the polymer has a molecular weight of 10 kDa to 900 kDa kDa, preferably 20 to 50 kDa for certain polysaccharides such as heparin, or 100 to 200 kDa for certain other molelcules, an example being chitosan.

Particularly preferred polymers are synthetic or homogeneous natural or biological sources of polysaccharides selected from the group of pyranoses, wherein monomers include (but are not limited to) dextrose, glucose, galactose, glucosamine, galactosamine, mannose, ribose, arabinose, xylose, lyxose, and amino sugars of the like.

Polymers may be provided in the form of peptides. A particularly preferred peptide is polyaspartic acid. As described herein, poly glutamic acid may be less preferred given that the spacing of the anionic side chains exceeds the preferred range of the invention of 4 to 6 angstroms. Other preferred peptides include polyserine, polythreonine, polyasparagine, polycysteic acic, polyselenocysteic acid, and D-configured amino acids of the same.

The polymer backbone may be aqueous soluble or insoluble.

In a particularly preferred embodiment the polymer contains a single monomer species having a length approximating the length of a glucose monomer (about 1.5 nm), or is a glucose monomer or derivative thereof having a length of about 1.5 nm, and wherein each monomer includes an anionic or electron rich group arranged so that each group is spaced apart by about 4 to 5 angstroms, and wherein the polymer contains about 100 to 400 monomers, preferably about 250 to 300 monomers, and/or has a molecular weight of about 40 to 60 kDa, preferably about 45 to 55 kDa.

In a preferred embodiment the polymer is a linear chain cellulose molecule wherein each monomer for presentation to an exosome outer membrane surface is functionalized with an anionic group or electron rich group, preferably a sulfate group.

It is not necessary that the entirety of the substrate surface should be covered by or contain the array of the exosome-binding ligands. In one embodiment, the substrate consists of an exosome or microvesicle binding region having an array of exosome-binding ligands on the region to enable exosomes or microvesicles to bind to the binding region. Other surfaces of a substrate may be engineered so as to preclude binding of exosomes. For example, these "non binding" regions may be constructed so that, in use, they do not present exosome-binding ligands to exosomes or microvesicles. Such an arrangement of exosome binding and non binding regions may be useful in the formation of devices for production, detection or monitoring of exosomes. Such devices may include microfluidic devices, or larger devices for cell culture or medical devices for clinical use.

The substrate may take the form of a range of shapes or configurations.

The surface of the substrate may be flat, curved, indented or porous. The surface may be formed within a device, tube or well, or on a bead.

In one embodiment, the substrate surface is brought into communication with one or more sensors for sensing the presence of, properties of, or size of exosomes or microvesicles bound to such substrate, using suitable nanotechnology analytical techniques such as atomic force microscopy, transmission electron microscopy (TEM), Auger emission spectrometry (AES) laser mass spectrometry, X-ray photon spectroscopy.

In another embodiment the substrate surface is in communication with measurement means to determine useful parameters of the exosome-substrate (or micro-vesicle-substrate) combination such as one or more of (i) presence or absence of exosome (and thereby number and density of exosomes) (ii) size of exosome (iii) conductivity of exosome (iv) a surface marker of exosome (v) rigidity of exosome (vi) charge of exosome or (vii) some other useful parameter through such means as one or more of (a) electrical probes, (b) imbedded laser (c) electric force microscopy (d) magnetic force microscopy (e) scanning gate microscopy or other suitable techniques. The substrate may form the measurement means.

The method of the invention utilizes substrates and exosome-binding ligands defined above to isolate microvesicles, in particular exosomes, from a biological source on the basis of charge. As described above, it is a surprising finding of the inventors that exosomes and micro-vesicles can be separated from other components of a biological fluid on the basis of charge, and in particular, on the basis of a positive charge of the exosome or microvesicle. On the basis of this finding, the inventors have utilized an ion exchange chromatography approach to the isolation of exosomes and microvesicles.

According to the invention the liquid containing the exosomes or microvesicles is contacted with the substrate in conditions enabling the binding of exosomes or microvesicles in the liquid to the exosome-binding ligands. This then binds exosomes or microvesicles to the substrate, which is the basis for the subsequent separation of exosomes or microvesicles from the liquid, as resulting from the separation of the substrate from the liquid.

The conditions for enabling binding of exosomes or microvesicles to the exosome-binding ligands generally require a consideration of salt content and pH of the liquid that contains the exosomes or microvesicles. Generally the pH of the liquid is defined by the pH stability of the exosomes or microvesicles, and this pH stability range is about 4 to 8

In some embodiments, the liquid containing the exosomes or microvesicles may be pre-processed prior to contact with the substrate. Such processing may include for example a pH adjustment to optimize the binding interaction with the exosome-binding ligands. For example, it may be necessary to adjust the pH of the solution to physiological pH level of 7.2 to 7.4. This ensures that the moieties on the exosomes or microvesicles that are bound by the exosome-binding ligands are cationic and able to bind to the anions or otherwise electron rich groups of the exosome-binding ligands.

Processing may also include salt adjustment, potentially salt minimization of the liquid, for example by a dialysis step, before contacting the liquid with the substrate.

Typically the liquid containing the exosomes or microvesicles will have a pH in the range of 7.2 to 7.4 and a salt content of 0.1 to 0.5M, preferably 0.15M and phosphate content of 0.01M prior to contact with the substrate.

Further processing may be required to remove cellular debris or contamination that may interfere with the binding of the exosomes or microvesicles to the exosome-binding ligands. This processing may involve centrifugation at 500 g, with or without filtration to about 0.22 micron.

In one embodiment, the liquid may be in the form of a biological fluid which is centrifuged to form a supernatant and a microvesicle-containing pellet and the supernatant is discarded and the pellet is re-suspended in an ion exchange binding buffer for contact with the substrate. Such a buffer generally has a pH in the range of 7.2 to 7.4 and a salt content in the range of 0.1M to 0.2M.

Filtration may also be employed to deplete microvesicles of a particular size from the liquid prior to contact of the liquid with the substrate. For example, the liquid may be fractionated to remove exosomes with a diameter greater than 100 nm prior to contact of the liquid with the substrate. Alternatively, this step could be performed at the completion of the elution of microvesicles from exosome-binding ligands (as described further below).

The liquid and substrate are brought into contact for a period of time sufficient to enable exosomes to bind to the exosome binding ligands. Generally this is from 1minute to 16 hours and can be in around 15 minutes. It could be less than 1 minute for example less than 30 seconds.

The contact of the liquid with the substrate may be established in a variety of formats. For example the liquid may be percolated through a solid resin or bead, captured, and the percolation and capture cycle repeated for a pre-determined number of cycles.

As discussed above, a particular advantage of the invention lies in the revelation that there is disparity among charged polymers, (particularly those derived from natural sources that have an inherent heterogeneity) vis a vis their capacity to bind to exosomes or microvesicles, and that it is possible to obtain significant improvements in binding efficiency by judicious selection of substrates or polymers according to the invention herein. In particular in the work described herein, the inventors have shown that polymers that perhaps might otherwise have been considered equally efficient for exosome or microvesicle binding—because in common they are all negatively charged at physiological pH—have varying levels of efficiency and that the various levels of binding efficiency can be explained by the arrangement of the negative charges presented to the outer membrane surface of an exosome or microvesicle.

In particular, as described herein, the inventors have determined that the overall isolation yield, which arises principally from differences in theoretical binding efficiency, ranges from about 4.3% (as observed for hyaluronic acid) to up to 98% (as observed for cellufine sulfate). Further, by determining a structural and binding model for the polymers tested for binding efficiency, the differences in binding efficiency have been explained in terms of the arrangement of anion and electron rich groups presented to the exosome outer membrane surface, enabling selection of optimal substrates or polymers for exosome binding, and in particular those more likely to provide a higher binding efficiency.

By implementing this work in an exosome or microvesicle isolation procedure, the invention enables a broader range of binding options than could otherwise be applied for obtaining an acceptable yield of exosomes or microvesicle. This is particularly useful where there are limits as to the pH or salt conditions that can be applied in a binding buffer.

Further the invention enables a more efficient binding procedure, potentially enabling shorter binding periods, or where multiple binding cycles would otherwise have been required, fewer binding cycles. These improvements enable the ion exchange approach to exosome or microvesicle isolation to be credibly translatable to high throughput processing, a manufacture practice that will ultimately be required to enable pharmaceutical scale production of exosomes.

A final step in the binding phase of the method is, as foreshadowed above, to separate the substrate from the liquid, thereby separating exosomes (which are bound to the exosome-binding ligands on the substrate) from the liquid. This separation may be achieved actively by removing the substrate from the liquid (for example by centrifuging a substrate in the form of beads), or passively by passing the liquid over the substrate, (thereby depleting exosomes from the liquid as the liquid separates from the substrate).

A particularly important advantage of the invention is that it enables elution of exosomes and/or microvesicles from a biological source so as to produce an eluate that consists primarily of exosomes and/or microvesicles and elution buffer. This is particularly important for regulating the quality control of the end product. In comparison, other approaches to date for isolation of exosomes result in the exosome being purified with a precipitating agent, for example, in the form of poly-ethylene glycol, or a polysaccharide or fragment thereof, together with an enzyme for degradation of the polysaccharide. These approaches require further manipulation of the end product to remove these contaminants, and this further manipulation, such as centrifugation or filtration, may deleteriously affect the exosomes.

It is a surprising finding of the invention that exosomes and microvesicles that have bound via higher affinity or higher avidity interactions to the substrates of the invention may be uniformly eluted from exosome-binding ligands, enabling release of the exosomes from the ligands. Specifically, as described herein, it has been found that selected but unrelated substrates, namely cellufine sulfate, chitosan and poly (methyl vinyl ether-maleic anhydride) have an improved exosome binding efficiency and the exosomes bound thereto may be commonly eluted by utilizing elution buffers having a range of salt concentrations or pH ranges within which exosomes remain stable.

Thus in one embodiment, the method includes the further step of eluting exosomes or microvesicles from the exosome-binding ligands to release the exosomes or microvesicles from the substrate after the substrate is separated from the liquid.

According to the invention, the exosomes or microvesicles may be eluted by contact of the substrate with an elution buffer. Typically an elution buffer has a salt content from about 0.5 to 4M, or from 0.5 to 2M, depending on the pH of the buffer system. This salt content establishes a preferential binding between the anionic species in the elution buffer and the outer membrane of the exosome or microvesicle resulting in elution.

In further embodiments, the salt content of the elution buffer may be the same as the binding buffer, and the elution buffer may have a higher pH than the binding buffer. This results in elution of the exosomes or microvesicle from the exosome-binding ligands as the pH of the buffer system approaches the isoelectric point of the moieties on the exosome or microvesicle which bind to the exosome binding ligands. Thus in one embodiment an elution buffer has a salt content of about 0.5 to 2M and a pH of about 7.2 to 7.4 pH units.

In another embodiment, the elution buffer may include oligomers of the polymer forming the substrate surface, said oligomers having a higher anionic charge or higher electropotential than the exosome-binding ligands on the polymer thereby resulting in elution of exosomes or microvesicles. For example, where the exosome binding ligands are provided on the substrate surface in the form of a cellulose sulfate polysaccharide, the elution buffer may include shorter chain cellulose oligomers having a higher amount of sulfation.

In another embodiment the elution buffer may include a competitive ligand that has a higher affinity than the exosome binding ligand on the substrate for an exosome or microvesicle. For example, an exosome can be eluted from a boronic acid polymer using an elution buffer containing an excess of a sugar, preferably fructose, which has a higher affinity than boronic acid for exosomes, thus eluting exosomes from the substrate.

In one embodiment, the elution buffer is applied to the substrate once only. In other embodiments the elution buffer may be continuously cycled for a pre-determined number of cycles.

In one embodiment, the method may include the further step of separating the released exosomes or microvesicles from the substrate. This step is particularly required where the exosomes or microvesicles remain in solution with the substrate at the completion of elution. One example is where the exosomes or microvesicles are eluted from exosome-binding ligands arranged on a substrate in the form of a bead and the bead is to be removed from the released exosomes or microvesicles. In other embodiments, the physical separation may result simply from the exosomes being eluted from the substrate, as for example may occur in a column chromatography.

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1

Exosome Isolation Using Polymer Based Substrates 1.1 Test Material

The test material used were cell culture conditioned medium derived from murine hypothalamic neuronal cell line GT 1-7 cultured in Opti-MEM complete culture media (Opti-MEM® Reduced Serum Medium+10% exosome depleted fetal calf serum+Penicillin-Streptomycin+GlutaMAX) for 48-72 hrs.

1.2 Test Method

Freshly harvested cell culture conditioned medium were centrifuged (500×g for 5 minutes) to remove cells and large debris, then the supernatant was filtered using 0.22 μm syringe filter to remove large vesicles and apoptotic bodies. The filtered conditioned medium was quantified for particle concentration using Nanoparticle Tracking analysis (NTA) on NanoSight NS300.

Table 1 describes a panel of polymer based substrates for which the binding and elution efficiency and overall isolation yields were determined.

Chitosan was 200 kDa (Biotin-) Chitosan (custom made). Viroadem beads were Ademtech Viro-Adembeads. Superdex® 75 was from Sigma Aldrich #S6657. BA-Magbeads were from Chemicell 1504-5 SiMAG-Boronic Acid magnetic particles. PEG-Control: Biotin-PEG24 (as control for 3-APBA/4-APBA which strictly speaking are Biotin-PEG24-3APBA and Biotin-PEG24-4APBA (custom made). Mag Bead Control was from Spherotech SVM-40-10 Avidin Coated Magnetic Particles. A Norgen Biotek Cell Culture Media Exosome Purification Kit (#60600) was used. Chitosan, heparin, 3-APBA, 4-APBA, PEG control and hyaluronic acid were Biotin-X coupled to Spherotech SVM-40-10 Avidin Coated Magnetic Particles.

The ligand immobilized on substrate at optimized concentration were incubated with 1 ml quantified test material for 5 hours at 4° C. on a tube rotator (100 rpm) to test the ability to affinity capture exosomes. The ligand immobilized-solid substrate was separated post-incubation and the concentration of the particles were determined in solution post-capture (unbound exosomes) using NTA on NanoSight NS300. The separated ligand immobilized-solid substrate bound to exosomes were incubated in elution solution overnight at 4° C. on a tube rotator (100 rpm) to elute bound exosomes. The ligand immobilized-solid substrate was separated post elution incubation and the concentration of particles were determined in solution using NTA on NanoSight NS300.

1.3 Data Acquisition

The particle concentration was determined using NTA on NanoSight NS300. The data acquisition strategy employed was to acquire 5×30 second videos in static mode operation. NanoSight software then analyzed the 5 independent 30 second video acquisitions to prepare an experimental report with the mean (+/−standard error) particle concentration data.

1.4 Test Read Outs

We measured particle concentration at three experimental stages
(i) Pre-affinity separation (i.e. particle concentration in test material before capture)
(ii) Post affinity capture in solution (i.e. particle concentration in test material after capture representing unbound exosomes)
(iii) Post elution (i.e. particle concentration in solution after elution of ligand captured particles)

1.5 Data Analysis Methodology

The test read out data obtained was used to determine four parameters:
ligand binding efficiency (i.e. number of particles in the test material captured by exposure to the ligand immobilized solid substrate)
ligand elution efficiency (i.e. proportion of that ligand captured particle that were eluted)
the overall process yield 1.6. Results In the optimized binding condition, cellulose sulfate ligand, in the form of cellufine sulfate, showed a theoretical binding efficiency of 77.90% with the number of theoretical bound particles being $1.31 \times 10^{10}$ (Table 1). The number of particles recovered after elution from cellufine sulfate beads was $1.64 \times 10^{10}$ with the elution efficiency being quantified by the instrument at 125% (Table 1). The overall process yield for cellufine sulfate ligand was 98% (Table 1). Note the elution efficiency of 125% was subject to a variety of quantification data variance due to operational and other factors. One would expect the actual elution efficiency to trend towards less than 100%.

Viroadembeads showed a theoretical binding efficiency of 66.13% with the number of theoretical bound particle being $1.11 \times 10_{10}$ (Table 1). In the elution conditions tested, we were able to elute 41° A of the particles captured by Viroadem beads with a mean size of 232.4 nm (Table 1). The overall process yield for Viroadembeads was 27% (Table 1).

Unexpectedly, the overall particle isolation yield for ultracentrifugation based exosome isolation was 7.5% (Table 1). This yield was drastically lower compared to the overall isolation yield observed with ligands reported in this invention. Nordin et al has reported exosome yield by ultracentrifugation to be 10% (Nordin et al., 2015). Furthermore, 4 L of adipose stem cell derived CM yielded 0.9 mg exosomes by ultracentrifugation, requiring 23 L CM and 276-280 hrs processing to generate a single human dose likely to be 5 mg. In comparison, ligand described in this invention with an exosome yield of 80% could generate a single human dose of 5 mg from less than 4 L of adipose stem cell derived CM with shorter processing time when processed in chromatography mode. This further highlights the superiority of the ligands described in this invention to isolate exosomes compared to the current gold standard isolation method of ultracentrifugation.

Example 2

Determining EMIT Structural and Functional Model

To determine the likelihood of optimal exosome binding among functionalized polymers, an in silico energy minimization protocol was followed. An oligomer representing a subsection of the polymer, which may range from a hexamer to a dodecamer in size, was drawn using the correct stereochemical configuration of ligands, where known, such as in the case of chitosan or cellufine sulfate, or defined, such as in the case of polyaspartic acid. Where the configuration was random or unknown, such as in the case of poly (methyl vinyl ether-maleic anhydride), then a random oligomeric structure was used in kind. The structures were then subjected to energy minimization calculations (MM+ or AMBER molecular mechanics model, HyperChem version 7.5), using a Polak-Ribiere descent function. The number of computational iterations needed to determine the energy minimum was typically 1000-2000 but if an energy minimum was not reached, the calculation was allowed to continue until such a minimum was achieved. At this point the arrangement was viewed from several angles and the positioning of the ligands was assessed in terms of mutual distance between, for instance, sulphur atoms in the case of sulfated polysaccharides, or anhydride carbonyl oxygens, in the case of poly (methyl vinyl ether-maleic anhydride. The secondary structure of the polymer in these cases illustrate arrangement of the backbone, which consists of the 6-12 monomer units, into a helical shape upon which the binding moieties project outwards. It should be understood that these energy-minimization calculations represent fractional subsections of the polymers, rather than the polymers as a whole, due both to software/processing limitations, and also to any variability in overall polymer size. Further, the MM+/AMBER type calculations are conducted in the absence of solvating molecules such as water or other components likely to be encountered in vivo or in a practical sense. Because these calculations are indeed performed only in the sense of the ligand-functionalized oligomers themselves, the method eliminates inconsistencies and unpredictable components that would be present in more complex media, and thus can be considered internally consistent. Moreover, the results obtained, with ligand spacing within the minimized structures, display a pattern consistent with observations of exosome binding efficiency.

Example 3

Predicted Structures of Cellufine Sulfate and Cellufine Phosphate

Cellufine sulfate is a synthetically derived cellulose sulfate particle, commercially available as Cellufine Sulfate (JNC Corporation, Japan). The synthesis method of cellufine sulfate preparation is part of European patent EP0171086 A2. In brief, non cross linked cellulose particle were developed from glucose polymer made of 250-300 glucose unit as raw polymer. Cellulose particle were then sulfated using sulfate reagents to derived cellulose sulfate beads (cellufine sulfate). The total sulfur content on the particles is 900 µg/g dry weight.

Figure 1B:
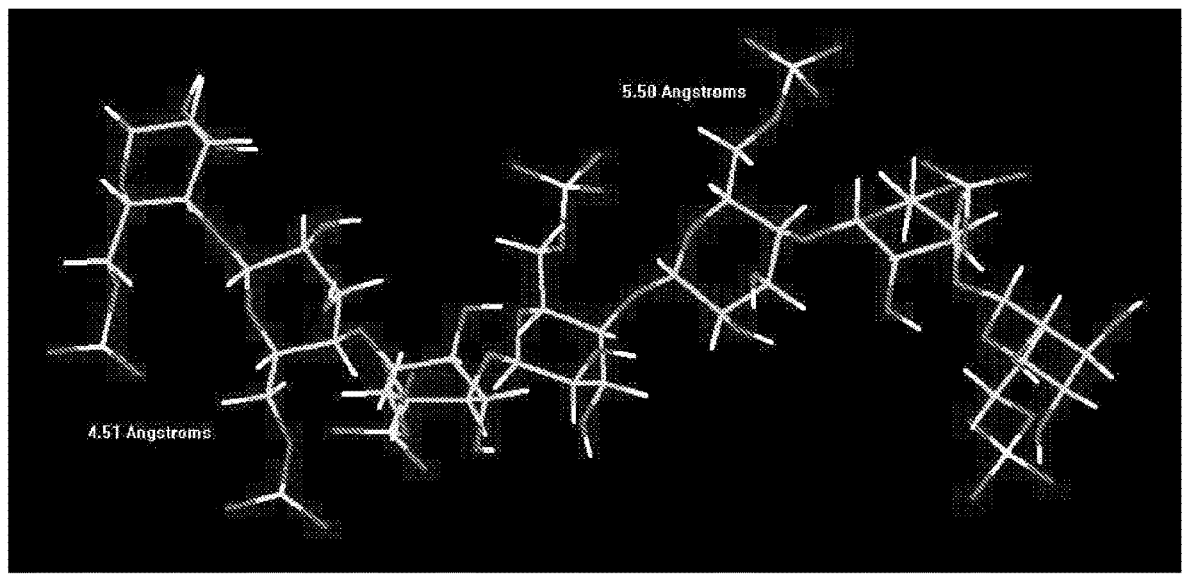

The cellufine sulfate heptamer model minimizes as shown (FIGS. 1(A) and 1(B)), projected end-on and side-on, with sample atom-atom measurements between neighboring sulfate oxygen species. The sulfate moieties (measured sulfur to neighboring sulfur) are approximately 6.7-7.9 Å apart, with the charged oxygens capable of moving within 4.5 Å (as indicated in the side-on projection). This model suggests that to bind exosomes, there must be both sufficient clearance (outward projection from the helix) and hydrogen bond-forming capability, such as between an alcohol moiety and an anionic or neutral, electron-rich oxygen. The exosome surface molecules to which ligands form hydrogen bonds are likely therefore to be hydrogen bond donors, such as alcohols, such as glycols within phospholipids or other major components of cell membranes. In this case a primary alcohol group ($CH_2OH$) is projected between two anionic groups, such as sulfates, forming a pincer-type hydrogen bond network, wherein the alcohol hydrogen can interact with two oxygen atoms at a time. The degenerate nature of the sulfate oxygens means that the probability of interaction is greater, (three per sulfate, six in total for a pair of sulfates) and thus increases the strength of the hydrogen bond network for binding. See FIGS. 1(A) and (B).

Cellufine phosphate, similarly, is a synthetically derived cellulose phosphate particle. It is also commercially available as Cellufine Phosphate (JNC Corporation, Japan).

Figure 1C:
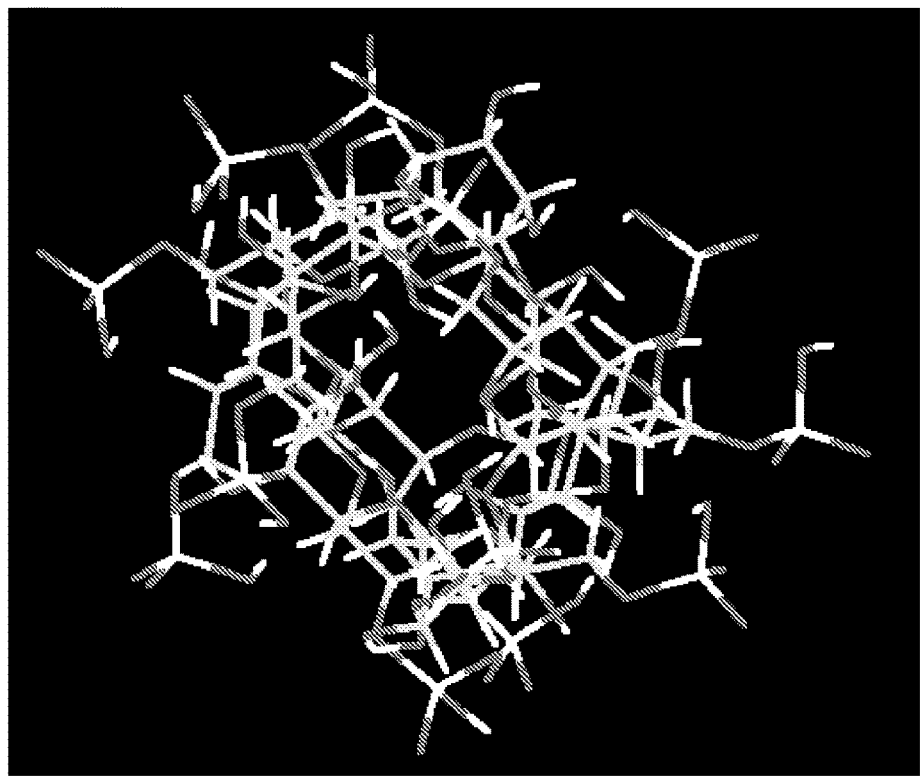
Figure 1D:
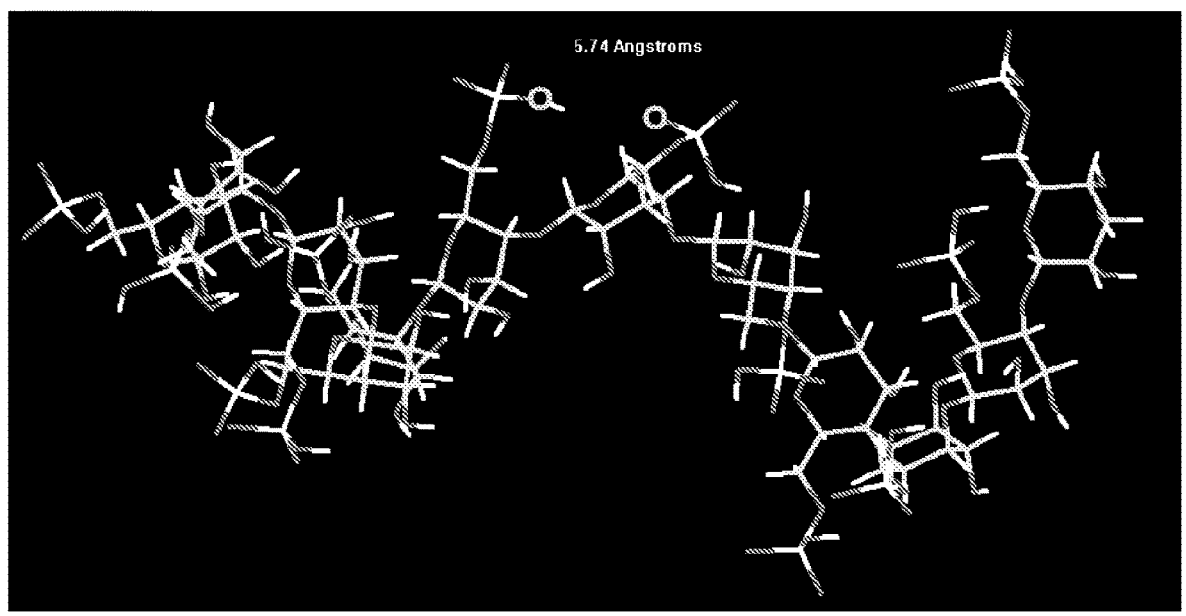

Represented as a dodecamer for illustrative purposes, FIGS. 1(C) and (D) indicate end-on and side-on depictions of the helical structure in the model. The model indicates the partially charged nature of the phosphate groups ($CH_2OP(O)(OH)_2$) as mono anions, effectively $CH_2OP(O)(OH)O^-$ consistent with the pH range of anticipated binding. In this case as well as for the cellufine sulfate, a primary alcohol group ($CH_2OH$) is projected between the anionic phosphates to form the pincer-type hydrogen bond network. The alcohol hydrogen can interact with two oxygen atoms at a time. The degenerate nature of the phosphate oxygens is similar to that of the sulfates, though the pH dependence of protonation degree of the phosphate will dictate the probability of interaction. As shown in FIGS. 1(C) and 1(D), two of the oxygens are degenerate and increase the strength of the hydrogen bond network for binding.

Example 4

Predicted Structure of poly (methyl vinyl ether-maleic anhydride)

The anionic polymer, poly (methyl vinyl ether-maleic anhydride) (poly(MVE-MA) is commercially available as Viroadembeads (Ademtech, France). The brief synthesis method for Viroadembeads is described below (Sakudo et al., 2009b). Small (300 nm in diameter) monozide magnetic particles (reducing sedimentation and offering a broad surface) with a high ferrite content (allowing for face separation under a magnetic field) prepared by the grafting of poly (MVE-MA) in dimethyl sulfoxide (DMSO)/phosphate buffer 5/95 solution for 3 hours at 37° C.

Figure 3:
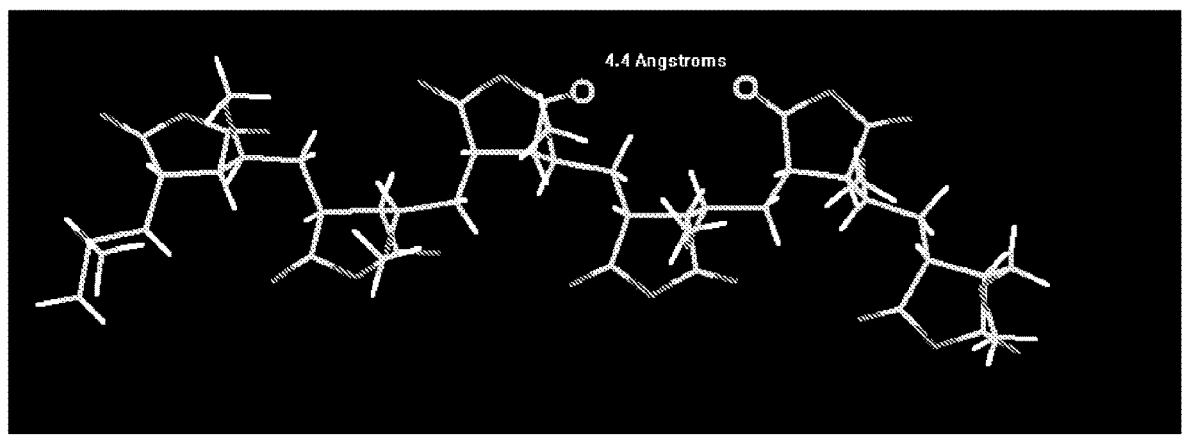
FIG. 3—Predicted structure of poly (methyl vinyl ether-maleic anhydride).

In the case of poly(methyl vinyl ether-maleic anhydride) (PMVEMA), the stereochemistry of substitution on both the furandione and backbone methoxy substitutions is random and undefined. For the purpose of obtaining an energy-minimized structure, a uniform and consistent stereochemical configuration was used, resulting in a sheet structure wherein alternating furandione moieties point away from the backbone. Separation between neighboring carbonyls, which could together act as hydrogen bond acceptors for interaction with phospholipids, is approximately 4.4 Å. See FIG. 3.

Example 5

Predicted Structure of Chitosan

Figure 2A:
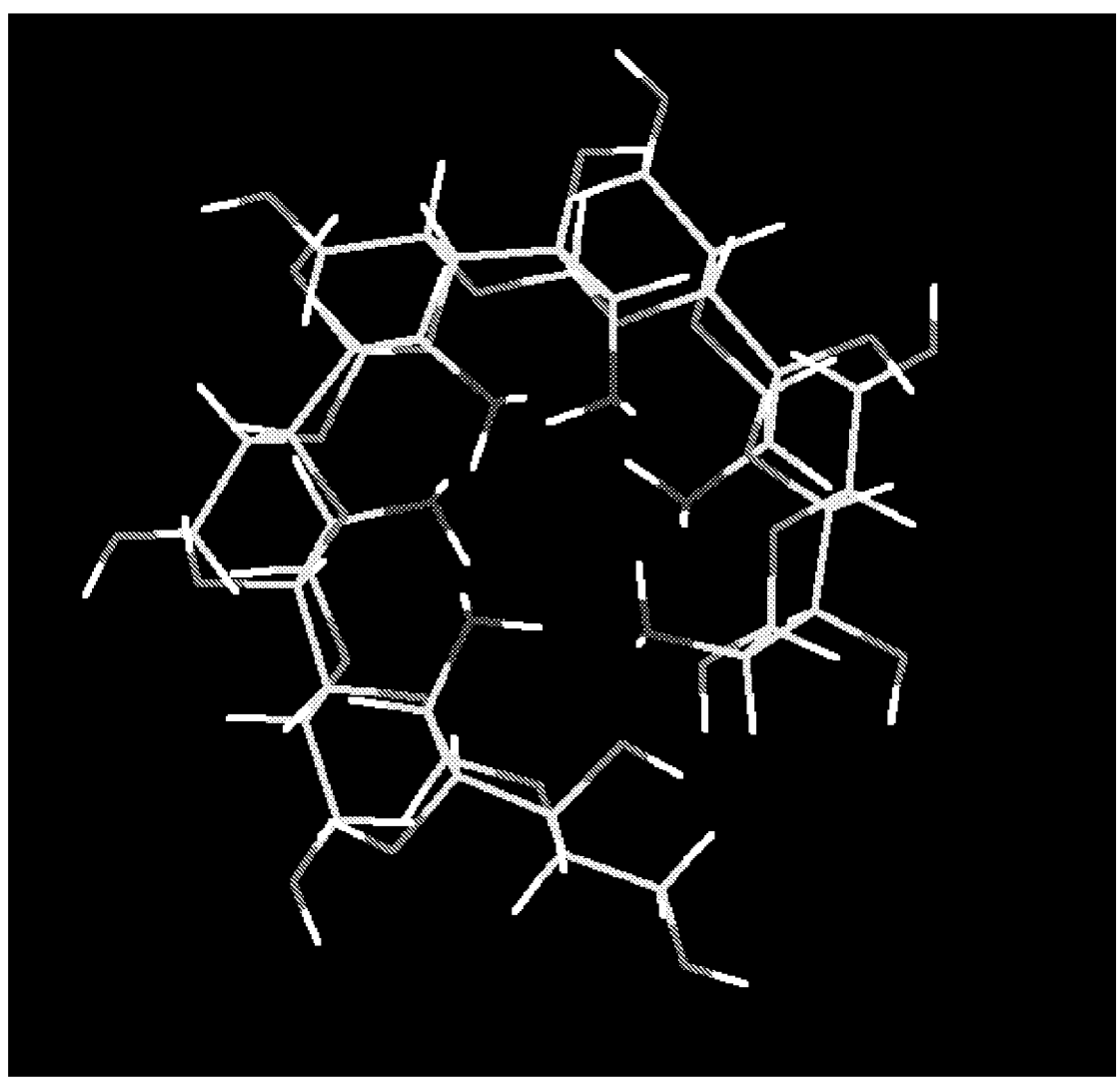
FIG. 2—Predicted structure of chitosan (A) projected end on view; and (B) side on view.
Figure 2B:
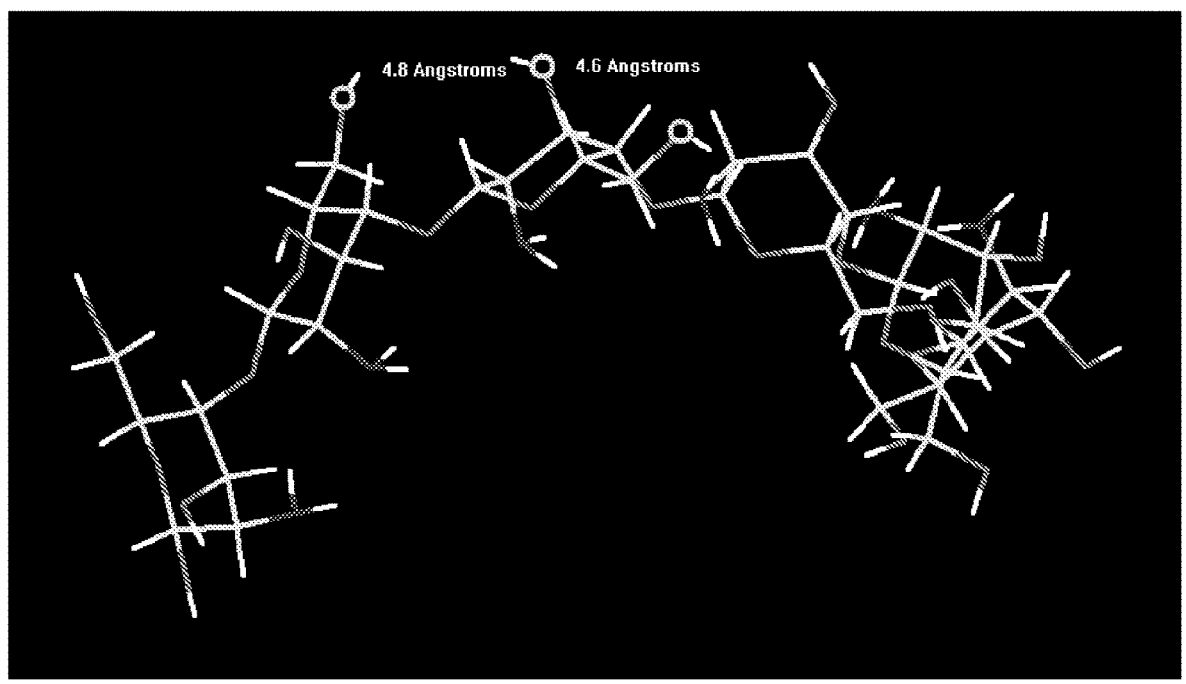

Chitosan, a natural polysaccharide resulting from the N-de-acetylation of chitin, contains 60-100% N-deacetylated monosaccharide units. The energy-minimized structure of chitosan forms a helix with the amino groups located towards the inner face, placing alcohol moieties projected outwards from the helix, as shown below, end-on. A side-on projection illustrates the position of the neighboring primary alcohol groups, proposed here as the binding moieties capable of interacting with the phospholipid of exosomes. These are roughly 4.6-5.0 Å apart arranged around the periphery of the helix. See FIGS. 2A and 2B.

Example 6

Predicted Structure of Heparin

Figure 4:
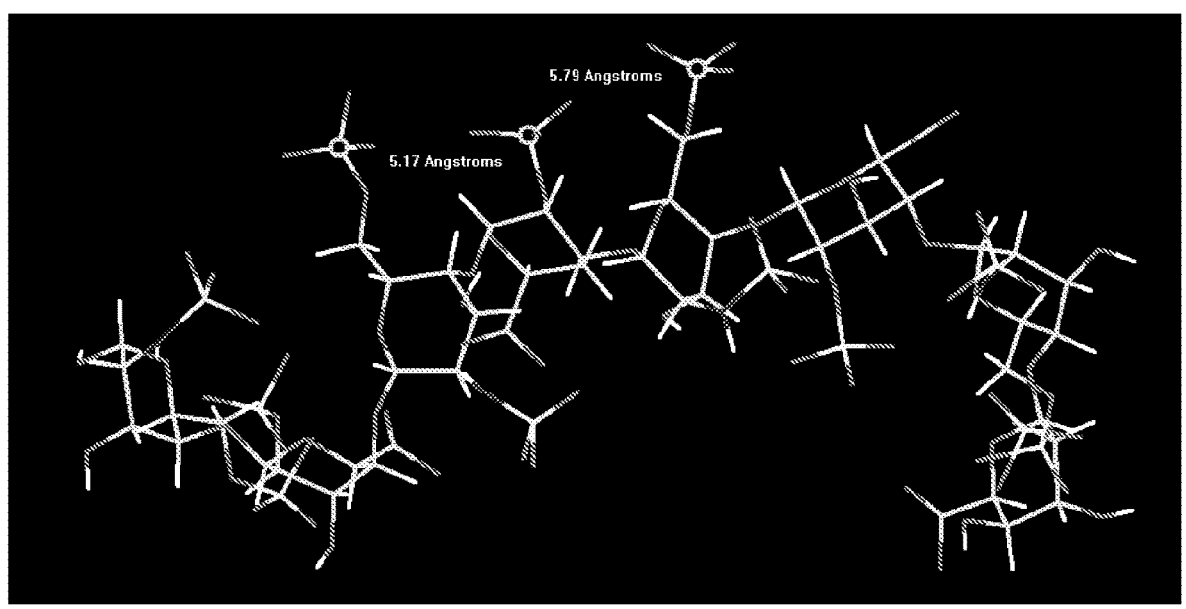
FIG. 4—Predicted structure of heparin.

Heparin, which is less sulfated than heparan, consists of glucuronic acid, galactosamine, and iduronic acid moieties. Heparin contains more iduronic acid than heparan, which carries more glucuronic acid monosaccharides. Therefore, an energy-minimized model of heparin is arbitrary since prediction of the geometry of binding moieties cannot be expected to be consistent throughout the polymeric structure. Assumptions are therefore predicated on an arbitrary arrangement of monosaccharide units, nevertheless the energy minimized structure also forms a helical superstructure, from which sulfate groups are projected outwards. Distances between neighboring sulfur atoms are between 5 and 6 Å as illustrated. Given that heparin would contain fewer sulfates than that depicted, it is possible that this would result in lowered binding efficiency than, for instance, cellufine sulfate, which contains a more consistent sequence of monosaccharide units. See FIG. 4.

Example 7

Predicted Structures for 3-APBA and 4-APBA

The compound 3-APBA refers to biotinylated (PEG-24)-3-aminophenylboronic acid, which, according to Table 1, bound exosomes poorly. Its 4-aminophenylboronic acid-based analogue (4-APBA in the above table) was also ineffective. Both compounds require sonicating prior to use, suggesting that in media they tend to fold in on themselves and form colloids or other suspensions that disfavor binding to exosomes.

The PEG control (simple polyethylene glycol) would have different physical characteristics in solution and would not associate in similar manner.

Figure 5:
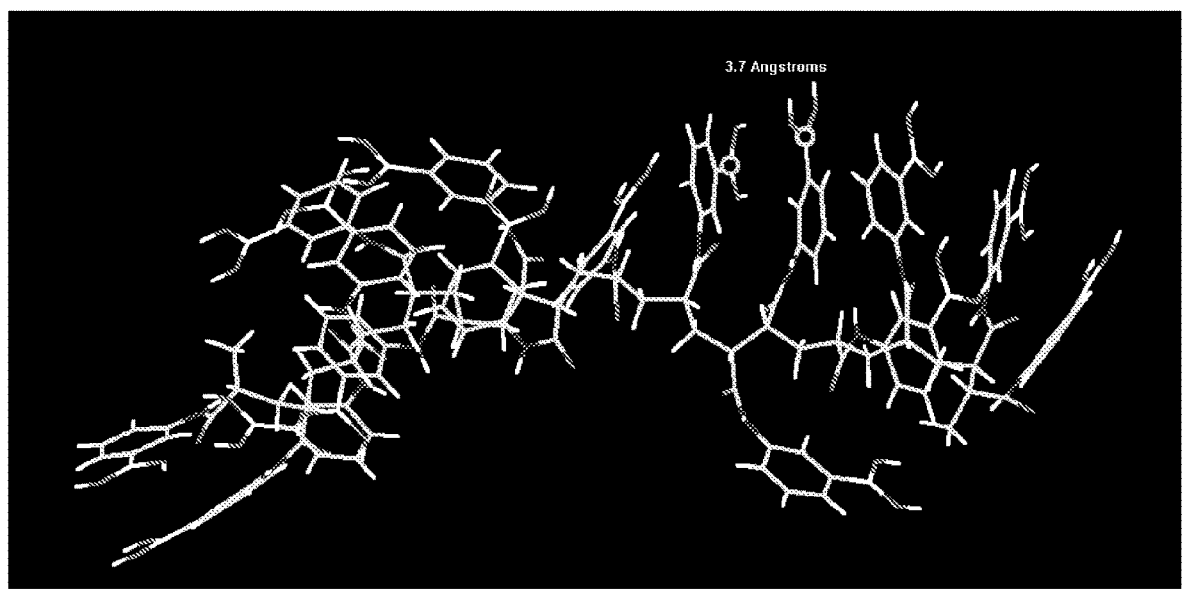
FIG. 5—Predicted structure for 3-APBA.

Organic polymers bearing equally spaced arrays of anionic groups, including boronic acids (such as poly-(3-acrylamidophenylboronic acid) occupy energy-minimized geometry that allows neighboring aryl groups to π-stack, with the anionic appendages arranged in fairly close proximity. This example, with random stereochemistry off the core polyacrylamide backbone, illustrates both features, with neighboring boron atoms less than 4 Å apart. See FIG. 5.

Example 8

Hyaluronic Acid Predicted Structure

Figure 6:
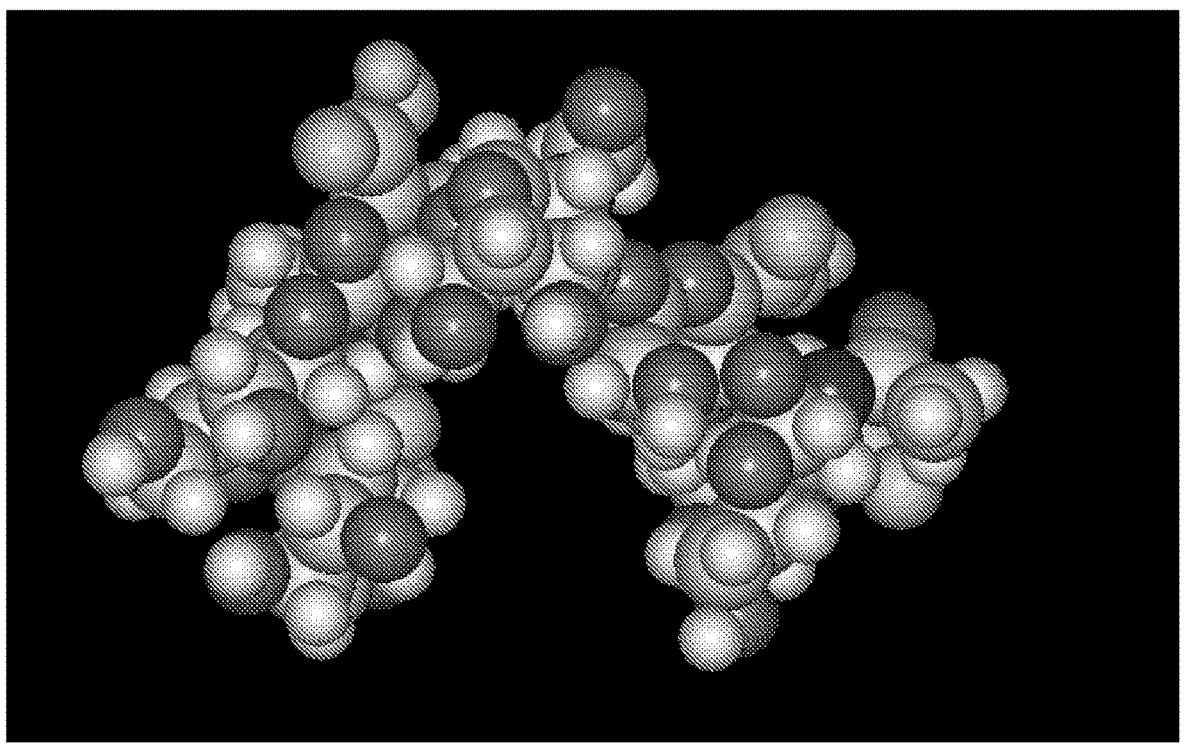
FIG. 6—Hyaluronic acid predicted structure.

Hyaluronic acid, which consists of alternating saccharide units connected through the 3- and 4-position, cannot easily form a tight helical structure wherein the negatively charged carboxylates form a similar conformation to those anionic groups present, for instance, in cellufine sulfate or heparin. The alternating disaccharides minimize to a less ordered, non-helical array, placing the carboxylates in relatively random positions. This lack of order may contribute to the compound's inability to bind exosomes efficiently. Here, the carboxylates are illustrated in green on a space-filling model to illustrate their lack of proximity to each other. See FIG. 6.

Example 9

Chondroitin Sulfate Predicted Structure

Figure 7:
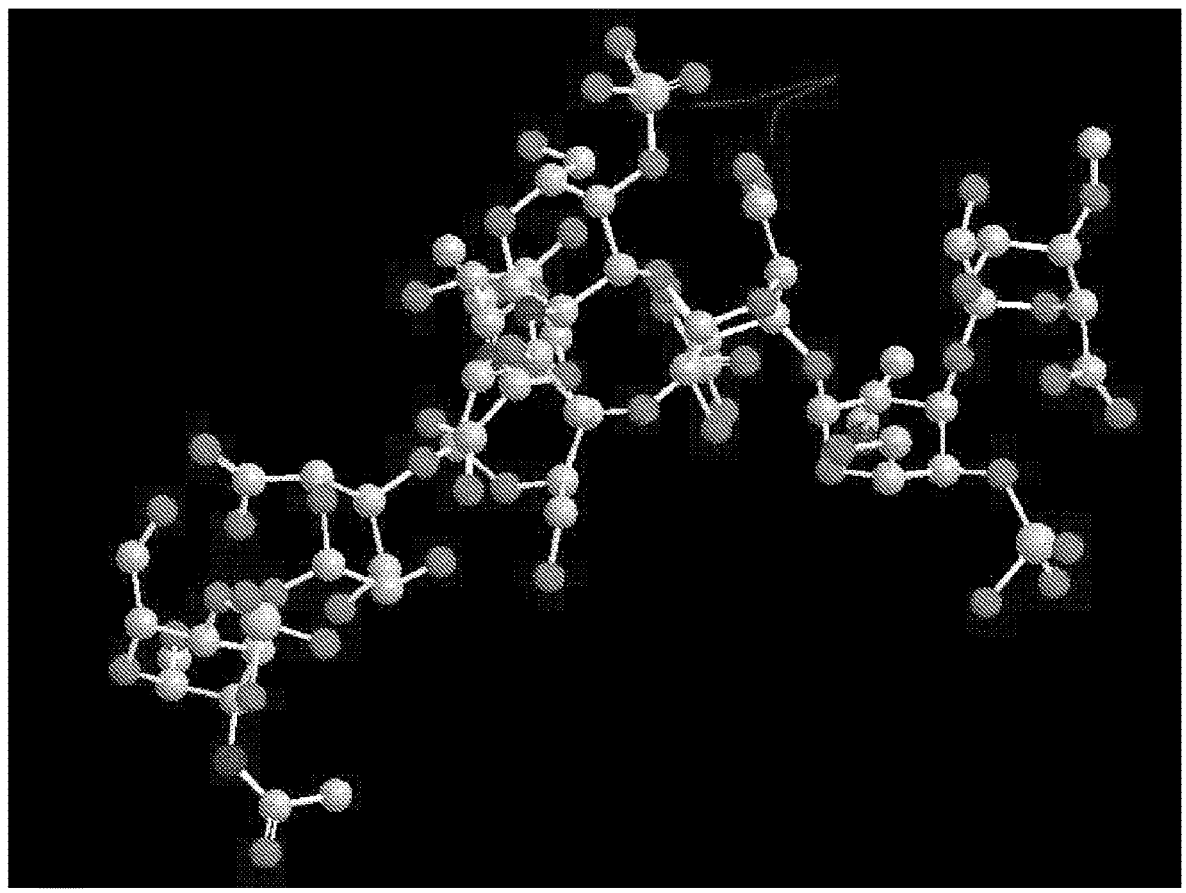
FIG. 7—Chondroitin sulfate predicted structure.

Chondroitin sulfate exists in various forms of 100 or more alternating glucuronic acid and N-acetylgalactosamine units, wherein the alternating monosaccharide units are joined at various positions. For this reason it is impossible to create a specific model by which one can predict its ability to bind exosomes. However, an MM2+-minimized model of an octamer illustrates that neighboring sulfate and carboxylate groups project outwards from the core backbone may be sufficiently exposed to facilitate interaction with phospholipids. See FIG. 7.

Example 10

Polyamino Acids Predicted Structure

Polyamino acids, another potential exosome binding ligand type, include polyglutamic acid, polyaspartic acid, polyserine, and the like.

Gamma-polyglutamic acid is predicted to adopt a sheet form with carboxylate groups situated perpendicularly to the backbone, approximately 12 Å apart: this distance between potential binding moieties may not be sufficient to permit efficient interaction with phospholipids. Therefore this polymer is predicted to be a low efficiency exosome binder.

Polyaspartic acid can be prepared in all L-form, all D-form, or as a configurational mixture by various synthetic methodologies. For illustrative purposes, an octamer of the poly-L-Asp is depicted as N-acetyl-Asp7NH2. In this case, the energy-minimized molecule appears as a series of alternating loops, upon which the carboxylates project outwards, with neighboring $CO_2$— groups between 4.5 and 5.0 Å apart (carbon to carbon distance). According to the structural model polyaspartic acid is predicted to be an efficient exosome binder.

Poly-β-asparagine derivatives can be prepared in all L-form, all D-form, or as a configurational mixture by various synthetic methodologies as described in example 11.

Based on this model, as well as observations of secondary structure in multiserine regions of naturally occurring proteins, synthetic polyserine would also be expected to exist in a series of alternating loops. In this case the proposed exosome binding moities, (electron rich alcohol moieties similar to those of chitosan), occupy similar neighboring distances to other exosome-binding polymers.

Sulfation of serines and other hydroxyl group bearing amino acids (e.g. tyrosine, threonine), to form polyserine sulfates, has been described in U.S. Pat. No. 4,444,682A (1984) by Rivier and Penke of the Salk Institute, by means of acetylsulfuric acid salts. Preparation of polyserine sulfate would thus deliver a peptide-like analogue of highly sulfated polysaccharides such as cellufine sulfate. The geometry of this molecule, by virtue of its asymmetry, adopts a more helical shape than that of the unsulfated polypeptide. As depicted in randomized side chain form (as would be seen in poly-D,L-Ser-sulfate) neighboring sulfate moieties arrange themselves outwards in a manner similar to that displayed by polysaccharides. Intersulfur atom distances are within similar range: 4.5-6.5 Å. See FIGS. 9 to 12.

Example 11(a)

Figure 11:
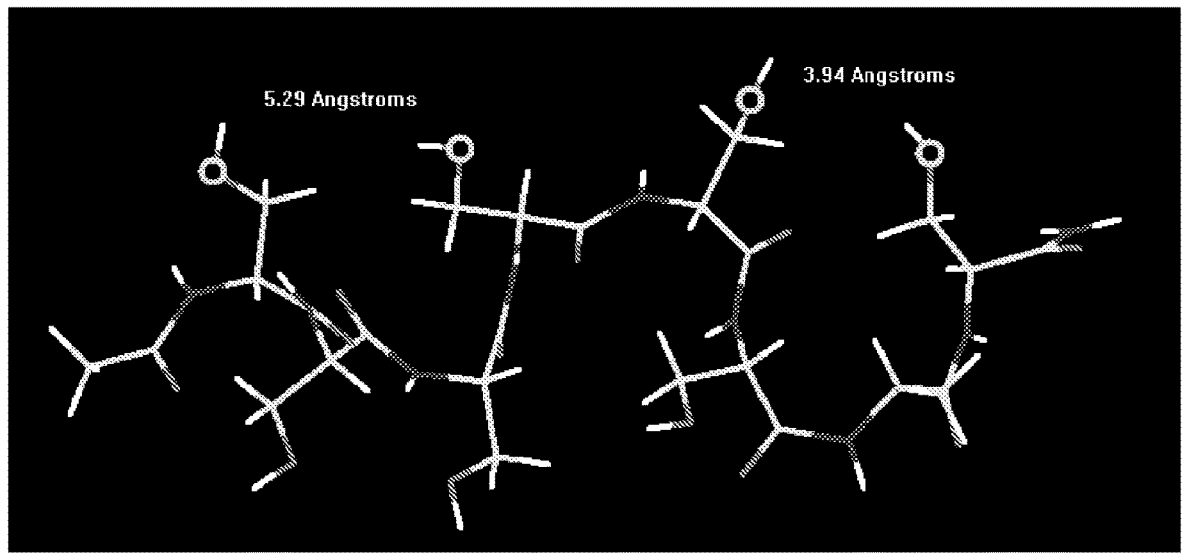
FIG. 11—Polyserine predicted structure.
Figure 11A:
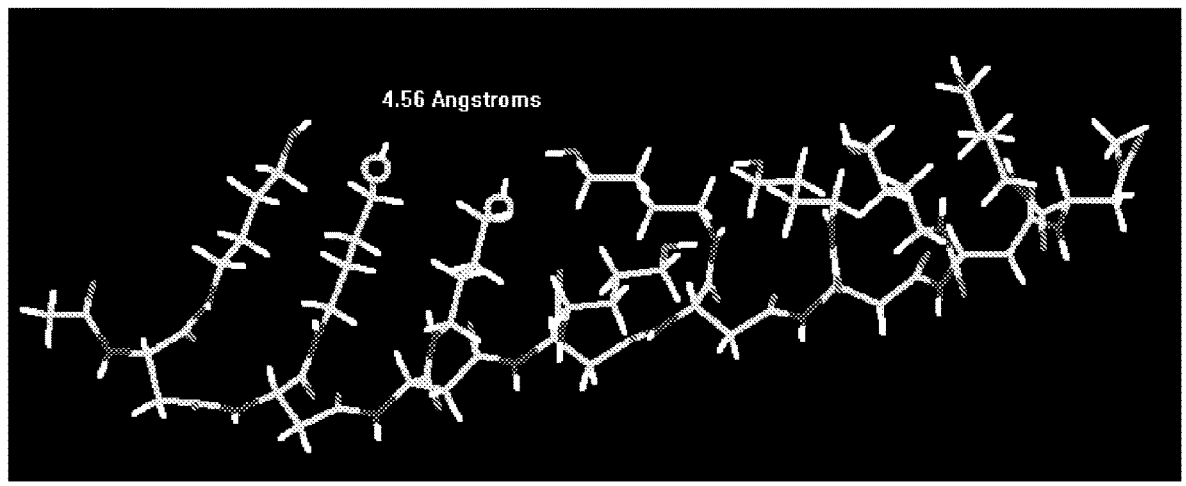
FIG. 11(A)—Biotin-C3-poly-4-hydroxybutyl-β-asparagine predicted structure
Figure 11B:
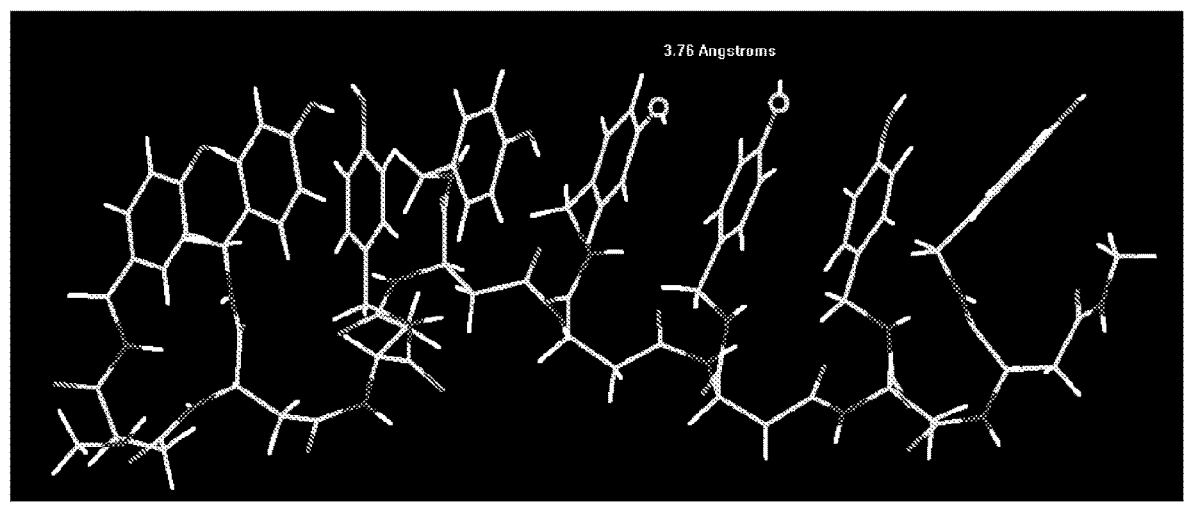
FIG. 11(B) biotin-C3-poly-4-hydroxybenzyl-β-asparagine predicted structure
Figure 12:
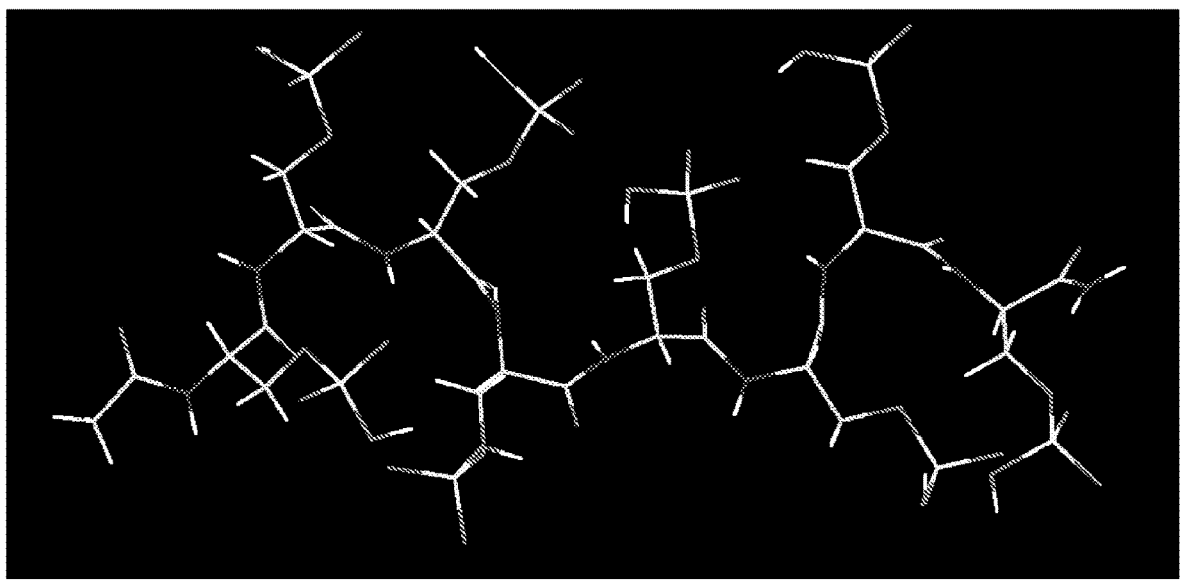
FIG. 12—Poly D L Serine sulfate predicted structure

Biotin-C3-poly-4-hydroxybutyl-β-asparagine and example 11(b) biotin-C3-poly-4-hydroxybenzyl-β-asparagine Synthesis is accomplished by treating the polymeric anhydride biotin C3-AspAn, (biotin C3-polysuccinimide) with 1-hydroxybutylamine or 4-phenoxyethylamine as indicated, resulting in the ring-opened polymeric β-asparagine derivatives. For illustrative purposes, an octamer of poly-β-1-hydroxybutylasparagine, FIG. 11(A), is used to indicate the energy-minimized conformation of example 11(a) and FIG. 11(B) illustrates the energy-minimized conformation of example 11(b). Both examples bound exosomes, illustrating the range of effective ligand separation.

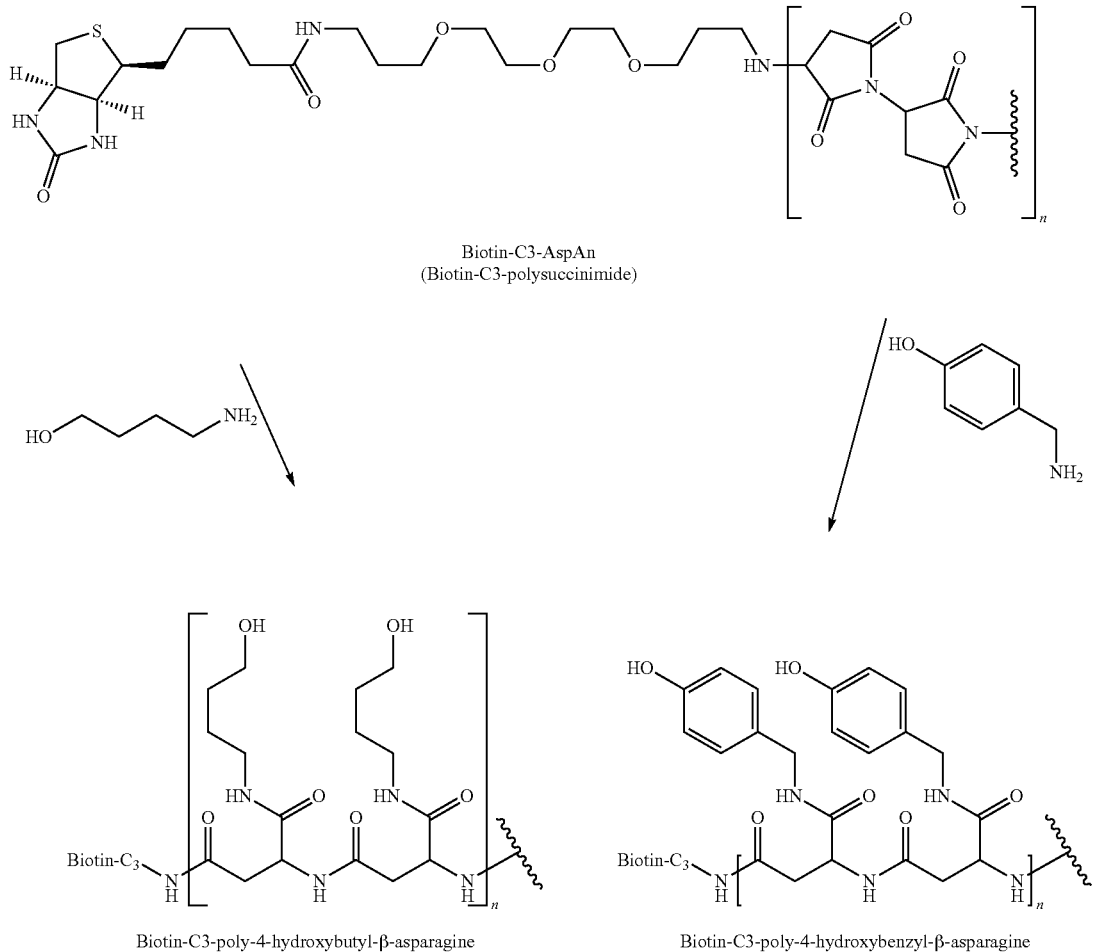

Biotin-C3-AspAn
(Biotin-C3-polysuccinimide)

Biotin-C3-poly-4-hydroxybutyl-β-asparagine

Biotin-C3-poly-4-hydroxybenzyl-β-asparagine

Example 12

General Structural Model

Figure 13:
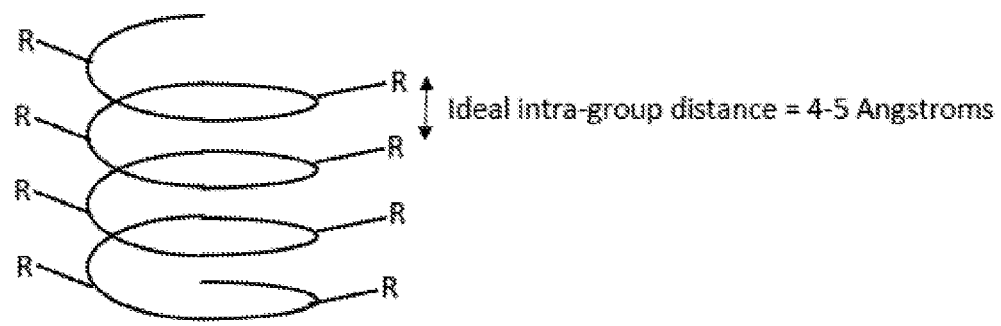
FIG. 13—General structural model.

A general model for polymer binding to exosomes can thus be represented as such: a helix or sheet with suitably spaced, projecting anionic or hydrogen-bonding capable groups extending outwards, where the backbone consists of a repeating template, and the anionic groups may be represented where $R=CO_2H$, $CH_2OH$, $CH_2OSO_3H$, $B(OH)_2$ and $CH2OP(O)(OH)2$, or those groups in ionized form as dictated by their relevant pKa, and the like to which the exosome is capable of binding. The model explains that polymers with high binding efficiency for exosomes bear anionic or electron rich groups wherein their mutual separation is between 4-5 Å. See FIG. 13.

Example 13

Polyvinyl Sulfate Predicted Structure

Figure 8:
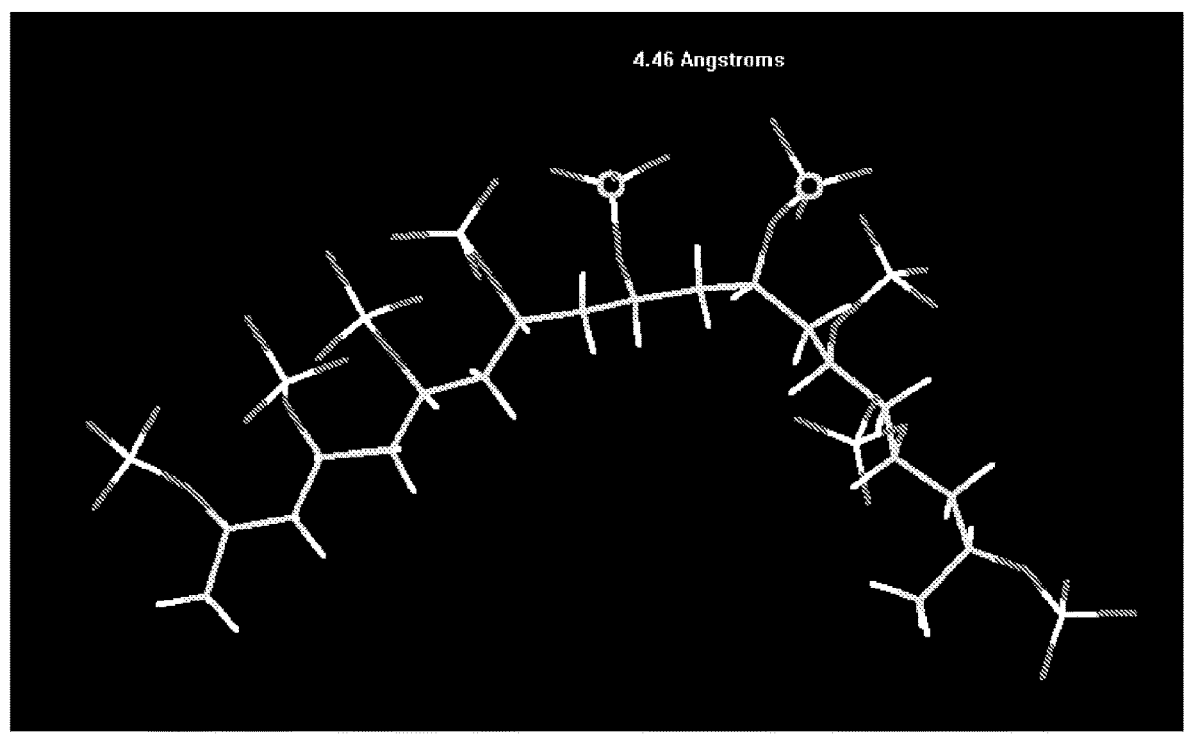
FIG. 8—Polyvinyl sulfate predicted structure.
Figure 9:
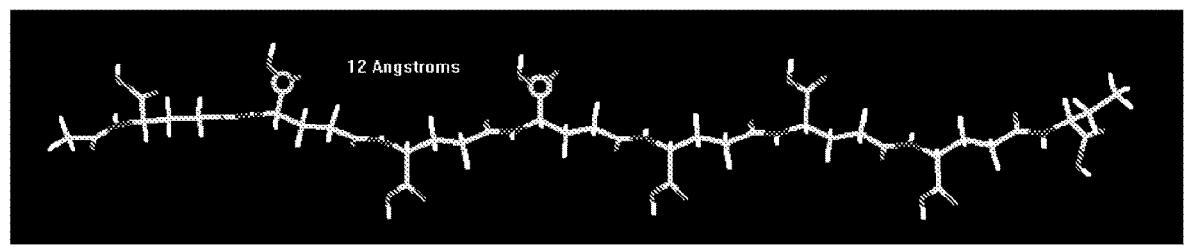
FIG. 9—Poly glutamic acid predicted structure.
Figure 10:
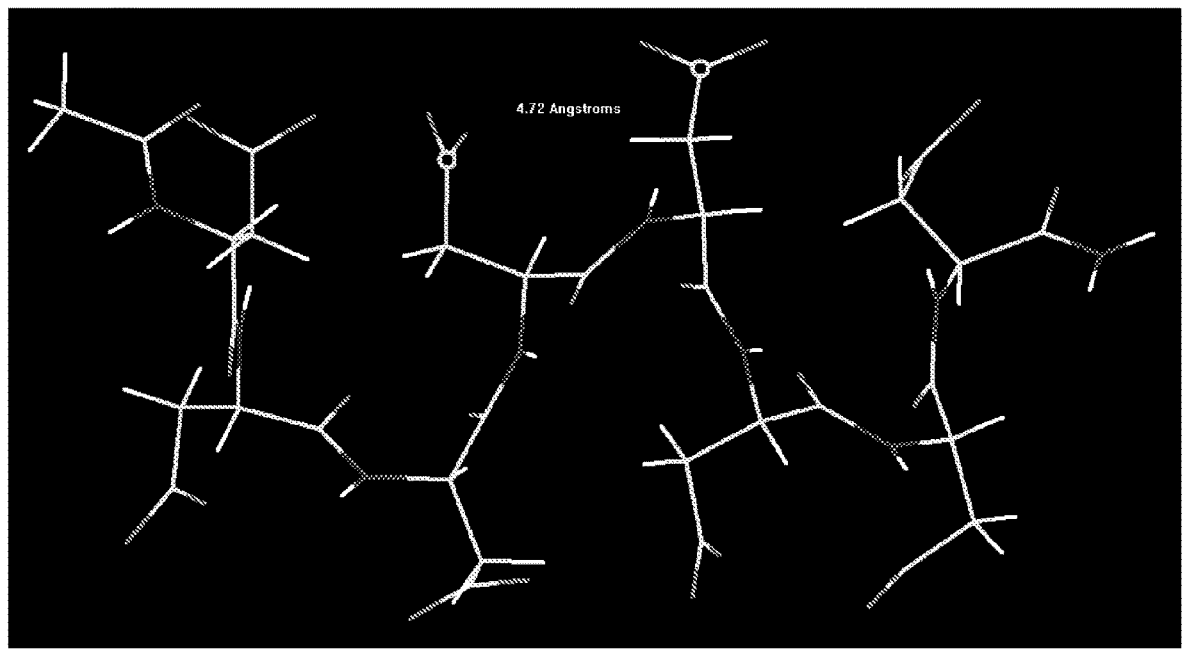
FIG. 10—Poly aspartic acid predicted structure.

The sulfur atoms in polyvinyl sulfate minimize themselves (in nonamer model) to about 4.2-4.5 angstroms apart. See FIG. 8.

Example 14

Prediction of Binding Efficiency of Exosome-Binding Ligands Based on Structural Model The general structural model at example 11 was utilised to predict the binding efficiency of exosome binding ligands, including those tested in the previous examples. The results are shown in Table 2.

REFERENCES

Raposo, G. and W. Stoorvogel, *Extracellular vesicles: exosomes, microvesicles, and friends.* J Cell Biol, 2013. 200(4): p. 373-83.

Urbanelli, L., Magini, A., Buratta, S., Brozzi, A., Sagini, K., Polchi, A., Tancini, B., and Emiliani, C. (2013). Signaling pathways in exosomes biogenesis, secretion and fate. Genes (Basel) 4, 152-170.

Rani, S., Ryan, A. E., Griffin, M. D., and Ritter, T. (2015). Mesenchymal Stem Cell-derived Extracellular Vesicles: Toward Cell-free Therapeutic Applications. Mol Ther 23, 812-823.

Chen, C., Skog, J., Hsu, C. H., Lessard, R. T., Balaj, L., Wurdinger, T., Carter, B. S., Breakefield, X. O., Toner, M., and Irimia, D. (2010). Microfluidic isolation and transcriptome analysis of serum microvesicles. Lab Chip 10, 505-511.

van der Pol, E., Hoekstra, A. G., Sturk, A., Otto, C., van Leeuwen, T. G., and Nieuwland, R. (2010). Optical and non-optical methods for detection and characterization of microparticles and exosomes. J Thromb Haemost 8, 2596-2607.

Greening, D. W., Xu, R., Ji, H., Tauro, B. J., and Simpson, R. J. (2015). A protocol for exosome isolation and characterization: evaluation of ultracentrifugation, density-gradient separation, and immunoaffinity capture methods. Methods Mol Biol 1295, 179-209.

Rider, M. A., Hurwitz, S. N., and Meckes, D. G., Jr. (2016). ExtraPEG: A Polyethylene Glycol-Based Method for Enrichment of Extracellular Vesicles. Sci Rep 6, 23978.

Heinemann, M. L., Ilmer, M., Silva, L. P., Hawke, D. H., Recio, A., Vorontsova, M. A., Alt, E., and Vykoukal, J. (2014). Benchtop isolation and characterization of functional exosomes by sequential filtration. J Chromatogr A 1371, 125-135.

Nordin, J. Z., Lee, Y., Vader, P., Mager, I., Johansson, H. J., Heusermann, W., Wiklander, O. P., Hallbrink, M., Seow, Y., Bultema, J. J., et al. (2015). Ultrafiltration with size-exclusion liquid chromatography for high yield isolation of extracellular vesicles preserving intact biophysical and functional properties. Nanomedicine 11, 879-883.

Sakudo, A., Baba, K., Tsukamoto, M., and Ikuta, K. (2009a). Use of anionic polymer, poly(methyl vinyl ether-maleic anhydride)-coated beads for capture of respiratory syncytial virus. Bioorg Med Chem Lett 19, 4488-4491.

TABLE 1

| Test Ligand | Theoretical number of bound exosomes (A-C) | EAL Binding efficiency (Theoretical % of bound exosomes = (A-C)*100/A) | Number of eluted exosomes (F) | EAL elution efficiency Theoretical % of eluted exosome (F*100/(A-C)) | Overall Isolation yield (% recovered exosomes = Number of eluted exosomes(F) *100/ number of input exosomes (A)) |
|---|---|---|---|---|---|
| Cellulose Sulfate 1 ml | $1.31 \times 10^{10}$ | 77.90% | $1.64 \times 10^{10}$ | 125% | 98% |
| Chitosan (500 ug) 5x107 | $8.75 \times 10^9$ | 48.60% | $8.75 \times 10^9$ | 100% | 48.60% |
| Viroadembeads 250 ul | $1.11 \times 10^{10}$ | 66.13% | $4.6 \times 10^9$ | 41% | 27% |
| Heparin (500 ug) 5x107 | $3.5 \times 10^9$ | 22% | $3.43 \times 10^9$ | 98% | 21.80% |
| Superdex 200 ul | Negative | | $1.8 \times 10^9$ | | 17.60% |
| 3-APBA (500 ug) 5x107 | $1.5 \times 10^9$ | 7.20% | $2.5 \times 10^9$ | 166% | 12% |
| 4-APBA (500 ug) 5x107 | Negative | | $3.35 \times 10^9$ | | 12% |
| BA- Magbeads (500 ul) | $4.2 \times 10^9$ | 15.10% | $3.33 \times 10^9$ | 79% | 12% |
| PEG-Control (for BA ligands) | $7.5 \times 10^9$ | 36.00% | $2.5 \times 10^9$ | 33.30% | 12% |
| Hyaluronic acid (500 ug) 5x107 | $5 \times 10^9$ | 22.70% | $7.8 \times 10^8$ | 15.60% | 4.30% |
| Mag Bead Control | $4.0 \times 10^9$ | 23.80% | $1.4 \times 10^9$ | 35% | 8.30% |
| Norgen (1 ml CM) | Not applicable | Not applicable | $7.92 \times 10^8$ | Not applicable | 7.70% |
| Norgen (7 ml CM) | Not applicable | Not applicable | $2.38 \times 10^9$ | Not applicable | 2.20% |
| Ultracentrifugation (1 ml CM) | Not applicable | Not applicable | $1.36 \times 10^9$ | Not applicable | 7.55% |

TABLE 2

Comparison of ligands LEAP tested and ligands predicted by EMIT structural model

| Ligand | Backbone | Binding Group | LEAP Test outcome* | EMIT prediction |
|---|---|---|---|---|
| Cellulose Sulfate | Polysaccharide | Sulfate | Positive | Binding |
| Cellulose phosphate | Polysaccharide | Phosphate | Not tested | Binding |
| Chitosan | Polysaccharide | —OH | Positive | Binding |
| Heparin | Polysaccharide | Sulfate | Positive | Less effective |
| Hyaluronic acid | Polysaccharide | Carboxylate | Negative | Less effective |
| Chondroitin sulfate | Polysaccharide | Sulfate and Carboxylate | Not tested | Binding |
| Dextran | Polysaccharide | —OH | Not tested | Less effective |
| Dextran sulfate | Polysaccharide | Sulfate | Not tested | Binding |
| poly(methyl vinyl ether-maleic anhydride) | Polymer synthetic | Carbonyls | Positive | Binding |
| $(PEG)_{24}$ Boronic Acid | Polymer synthetic | Boronic acid | Negative | No Binding |
| Boronic Acid Polymer | Polymer synthetic | Boronic acid | Not tested | Binding |
| Polyaspartic acid | Peptide | Carboxylate | Not tested | Binding |
| Substituted poly-β-asparagine | Peptide | —OH | Positive | Binding |
| Polyserine | Peptide | —OH | Not tested | Binding |
| Polyserine sulfate | Peptide | Sulfate | Not tested | Binding |

Note:
*Ligands with 25% or more overall isolation yield in the LEAP testing were considered as positive

The invention claimed is:

1. A method for obtaining a composition or an isolate of exosomes or microvesicles comprising:
providing a liquid that includes exosomes or microvesicles;
providing a substrate having a surface, the surface having an array of exosome-binding ligands, wherein the array is formed from one or more polymers having the exosome-binding ligands, wherein at least 60% of ligands of the array are spaced between 5 and 10 angstroms apart from another ligand of the array;
wherein each ligand is in the form of an anionic group at pH 4-8; and
wherein the array of exosome-binding ligands enables exosomes or microvesicles to bind to the substrate;
contacting the liquid with the substrate in conditions enabling the binding of exosomes or microvesicles to the exosome-binding ligands;
separating the substrate from the liquid;
eluting exosomes or microvesicles from the exosome-binding ligands to release the exosomes or microvesicles from the substrate after the substrate is separated from the liquid;
separating the released exosomes or microvesicles from the substrate;
thereby obtaining a composition or isolate of exosomes or microvesicles.

2. The method of claim 1, wherein the one or more polymers include a monomer species having at least one exosome-binding ligand.

3. The method of claim 2, wherein at least 25% of the monomers of the one or more polymers includes an exosome-binding ligand.

4. The method of claim 2, wherein all monomers of the one or more polymers have an exosome-binding ligand.

5. The method of claim 1, wherein at least 60% of ligands of the array are spaced between 6 and 10 angstroms apart from another ligand of the array.

6. The method of claim 1, wherein two or more monomeric species include an exosome-binding ligand.

7. The method of claim 1, wherein part of the substrate surface includes the array.

8. The method of claim 1, wherein the polymer is selected from the group comprising: polysaccharide; polyethylene terephthalate; peptide; nucleic acid; organic molecules; and combinations thereof.

9. The method of claim 8, wherein the polymer is a polysaccharide or peptide.

10. The method of claim 9, wherein the polymer is a peptide selected from the group comprising: polyaspartic acid, polyserine, polythreonine, polyasparagine, and combinations thereof.

11. The method of claim 9, wherein the polysaccharide is selected from the group comprising: pyranoses and amino sugars, wherein the pyranose comprises monomers selected from: dextrose, glucose, galactose, glucosamine, galactosamine, mannose, ribose, arabinose, xylose, lyxose, and combinations thereof.

12. The method of claim 9, wherein the peptide is selected from the group comprising:
polyaspartic acid, polyserine, polythreonine, polyasparagine, polycysteic acic, polyselenocysteic acid, D-configured amino acids of the same, and combinations thereof.

13. The method of claim 8, wherein the polymer is an organic molecule selected from the group comprising: polyethers, (PEGS), sulfated polyvinyl alcohols, polyphenols, polyphenylboronic acids, polyaromatics, polyheteroaromatics, and combinations thereof.

14. The method of claim 1, wherein the polymer is a synthetic polymer.

15. The method of claim 1, wherein the one or more polymers form the substrate.

16. The method of claim 1, wherein the one or more polymers are coupled to the substrate.

17. The method of claim 1, wherein the one or more polymers are soluble in the liquid.

18. An apparatus including a substrate according to claim 1 and enabling the execution of a method according to claim 1.

19. The method of claim 1, wherein the array is planar and includes a region of exosome-binding ligands having a density of 2 to 4 ligands per $nm^2$.

20. The method of claim 19, wherein the array includes a region of exosome-binding ligands having a density of 3 to 4 ligands per $nm^2$.

21. The method of claim 1, wherein the polymer has a molecular weight of 10 to 900 kDa.

22. The method of claim 1, wherein the polymer contains 100 to 400 monomers.

23. The method of claim 1, wherein the anionic group is selected from the group comprising: sulfates, selenates, phosphates, phosphonates, phosphinates, sulfated alcohols, carboxylate groups, acylsulfonamides and combinations thereof.

24. The method of claim 1, wherein the anionic group is selected from the group comprising: $CO_2H$, $CH_2OSO_3H$, $B(OH)_2$, $CH_2OP(O)(OH)_2$, ionized forms thereof, and combinations thereof.

25. The method of claim 1, wherein the polymer is selected from the group comprising:
cellulose sulfate, cellulose phosphate, chitosan, chondroitin sulfate, dextran sulfate, poly(methyl vinyl ether-maleic anhydride), boronic acid polymer, polyaspartic acid, substituted poly-β-asparagine, polyserine, polyserine sulfate and combinations thereof.

26. The method of claim 1, wherein the polymer is selected from the group comprising:
cellulose sulfate, dextran sulfate, polyacrylamide sulfoisobutyl, and combinations thereof.

27. The method of claim 1, wherein the polymer is selected from the group comprising:
cellulose sulfate, cellufine sulfate, dextran sulfate and combinations thereof.

* * * * *